US007901890B2

(12) United States Patent
Dahl et al.

(10) Patent No.: US 7,901,890 B2
(45) Date of Patent: *Mar. 8, 2011

(54) METHODS AND OLIGONUCLEOTIDE DESIGNS FOR INSERTION OF MULTIPLE ADAPTORS EMPLOYING SELECTIVE METHYLATION

(75) Inventors: Fredrik Dahl, Menlo Park, CA (US); Radoje Drmanac, Los Altos Hills, CA (US); Andrew Sparks, Los Gatos, CA (US)

(73) Assignee: Complete Genomics, Inc., Mountain View, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 12/265,593

(22) Filed: Nov. 5, 2008

(65) Prior Publication Data

US 2009/0203551 A1    Aug. 13, 2009

Related U.S. Application Data

(60) Provisional application No. 60/985,441, filed on Nov. 5, 2007.

(51) Int. Cl.
*C12Q 1/68* (2006.01)
*C12P 19/34* (2006.01)

(52) U.S. Cl. .............................. 435/6; 435/91.2; 435/91.4

(58) Field of Classification Search ........................ None
See application file for complete search history.

(56) References Cited

U.S. PATENT DOCUMENTS

| | | | | |
|---|---|---|---|---|
| 4,719,179 A | 1/1988 | Baranay | ..................... | 435/172.1 |
| 4,883,750 A | 11/1989 | Whiteley | ............................ | 435/6 |
| 5,091,302 A | 2/1992 | Newman | ............................ | 435/6 |
| 5,124,246 A | 6/1992 | Urdea | ............................ | 435/6 |
| 5,143,854 A | 9/1992 | Pirrung | ........................ | 436/518 |
| 5,202,231 A | 4/1993 | Drmanac | ........................... | 435/6 |
| 5,354,668 A | 10/1994 | Auerbach | ..................... | 435/91.1 |
| 5,403,708 A | 4/1995 | Brennan | ............................ | 435/6 |
| 5,426,180 A | 6/1995 | Kool | ............................ | 536/25.3 |
| 5,427,930 A | 6/1995 | Birkenmeyer | ............. | 435/91.52 |
| 5,474,796 A | 12/1995 | Brennan | ....................... | 427/2.13 |
| 5,508,169 A | 4/1996 | Deugau | ............................ | 435/6 |
| 5,525,464 A | 6/1996 | Drmanac | ........................... | 435/6 |
| 5,632,957 A | 5/1997 | Heller | ........................... | 422/68.1 |
| 5,641,658 A | 6/1997 | Adams | ......................... | 435/91.2 |
| 5,648,245 A | 7/1997 | Fire | ................................ | 435/91.1 |
| 5,710,000 A | 1/1998 | Sapolsky | ........................... | 435/6 |
| 5,714,320 A | 2/1998 | Kool | ................................ | 435/6 |
| 5,728,524 A | 3/1998 | Sibson | ............................ | 435/6 |
| 5,744,305 A | 4/1998 | Fodor | ............................ | 435/6 |
| 5,800,992 A | 9/1998 | Fodor | ............................ | 435/6 |
| 5,854,033 A | 12/1998 | Lizardi | ......................... | 435/91.2 |
| 5,866,337 A | 2/1999 | Schon | ............................ | 435/6 |
| 5,871,921 A | 2/1999 | Landegren | ...................... | 435/66 |
| 5,888,737 A | 3/1999 | DuBridge | ........................ | 435/6 |
| 5,994,068 A | 11/1999 | Guilfoyle | ......................... | 435/6 |
| 6,004,755 A | 12/1999 | Wang | ............................ | 435/6 |
| 6,013,445 A | 1/2000 | Albrecht | ........................... | 435/6 |
| 6,045,994 A | 4/2000 | Zabeau | ............................ | 435/6 |
| 6,077,668 A | 6/2000 | Kool | ............................ | 435/6 |
| 6,096,880 A | 8/2000 | Kool | ............................ | 536/25.3 |
| 6,124,120 A | 9/2000 | Lizardi | ......................... | 435/91.2 |
| 6,136,537 A | 10/2000 | Macevicz | .......................... | 435/6 |
| 6,143,495 A | 11/2000 | Lizardi | ............................ | 435/6 |
| 6,143,527 A | 11/2000 | Pachuk | ........................ | 435/91.1 |
| 6,210,891 B1 | 4/2001 | Nyren | ............................ | 435/6 |
| 6,210,894 B1 | 4/2001 | Brennan | ............................ | 435/6 |
| 6,218,152 B1 | 4/2001 | Auerbach | ..................... | 435/91.2 |
| 6,221,603 B1 | 4/2001 | Mahtani | ............................ | 435/6 |
| 6,255,469 B1 | 7/2001 | Seeman | ....................... | 536/23.1 |
| 6,258,539 B1 | 7/2001 | Hunkapiller et al. | ............. | 435/6 |
| 6,261,808 B1 | 7/2001 | Auerbach | ..................... | 435/91.1 |
| 6,270,961 B1 | 8/2001 | Drmanac | .......................... | 435/6 |
| 6,274,320 B1 | 8/2001 | Rothberg et al. | ................. | 435/6 |
| 6,274,351 B1 | 8/2001 | Peponnet | ....................... | 435/91.1 |
| 6,284,497 B1 | 9/2001 | Sabanayagam et al. | ..... | 435/91.2 |
| 6,287,824 B1 | 9/2001 | Lizardi | ......................... | 435/91.2 |
| 6,291,183 B1 | 9/2001 | Pirrung et al. | ..................... | 435/6 |
| 6,297,006 B1 | 10/2001 | Drmanac et al. | .................. | 435/6 |
| 6,297,016 B1 | 10/2001 | Egholm et al. | .................... | 435/6 |
| 6,306,597 B1 | 10/2001 | Macevicz | .......................... | 435/6 |
| 6,309,824 B1 | 10/2001 | Drmanac | .......................... | 435/6 |
| 6,316,229 B1 | 11/2001 | Lizardi | ......................... | 435/91.1 |
| 6,329,150 B1 | 12/2001 | Lizardi | ............................ | 435/6 |
| 6,344,329 B1 | 2/2002 | Lizardi | ............................ | 435/6 |

(Continued)

FOREIGN PATENT DOCUMENTS

| | | |
|---|---|---|
| JP | 4-262799 | 9/1992 |
| JP | 4-304900 | 10/1992 |
| WO | WO 95/09248 | 4/1995 |
| WO | WO 01/62982 | 8/2001 |
| WO | WO 02/074988 | 9/2002 |
| WO | WO 03/012119 | 2/2003 |
| WO | WO 2004/072294 | 8/2004 |
| WO | WO 2004/076683 | 9/2004 |
| WO | WO 2005/040425 | 5/2005 |
| WO | WO 2005/047523 | 5/2005 |

(Continued)

OTHER PUBLICATIONS

Blanco et al., "Highly efficient DNA synthesis by the phage phi 29 DNA polymerase," J. Biol. Chem., v. 264, issue 15, p. 8935-8940 (1989).

Brenner et al, "Gene Expression Analysis by Massivly Parallel Signature Sequencing (MPSS) on Microbead Arrays," Nature Biotechnology, v. 18, p. 630-634 (2000).

Callow, Matthew J., et al. "Selective DNA amplification from complex genomes using universal double-sided adapters," Nucleic Acids Research, vol. 32, No. 2, e21, p. 1-6, (Jan. 2004).

(Continued)

*Primary Examiner* — Kenneth R. Horlick
*Assistant Examiner* — David C Thomas
(74) *Attorney, Agent, or Firm* — Robin M. Silva; Gargi Talukder; Morgan Lewis & Bockius LLP

(57) ABSTRACT

Aspects described and claimed herein provide methods to insert multiple DNA adaptors into a population of circular target DNAs at defined positions and orientations with respect to one another. The resulting multi-adaptor constructs are then used in massively-parallel nucleic acid sequencing techniques.

17 Claims, 11 Drawing Sheets

U.S. PATENT DOCUMENTS

| | | | |
|---|---|---|---|
| 6,346,413 B1 | 2/2002 | Fodor | 435/287.2 |
| 6,355,432 B1 | 3/2002 | Fodor | 435/6 |
| 6,401,267 B1 | 6/2002 | Drmanac | 435/6 |
| 6,403,320 B1 | 6/2002 | Read | 435/6 |
| 6,413,722 B1 | 7/2002 | Arnold | 435/6 |
| 6,432,360 B1 | 8/2002 | Church | 422/68.1 |
| 6,472,156 B1 | 10/2002 | Wittwer | 435/6 |
| 6,491,871 B1 | 12/2002 | Fodor | 422/63 |
| 6,500,620 B2 | 12/2002 | Yu | 435/6 |
| 6,514,768 B1 | 2/2003 | Guire | 436/518 |
| 6,534,293 B1 | 3/2003 | Baranay | 435/91.2 |
| 6,558,928 B1 | 5/2003 | Landegren | 435/91.1 |
| 6,573,369 B2 | 6/2003 | Henderson | 536/23.1 |
| 6,576,448 B2 | 6/2003 | Weissman | 435/91.2 |
| 6,589,726 B1 | 7/2003 | Butler | 435/4 |
| 6,610,481 B2 | 8/2003 | Koch | 435/6 |
| 6,620,584 B1 | 9/2003 | Chee | 435/6 |
| 6,632,609 B2 | 10/2003 | Lizardi | 435/6 |
| 6,653,077 B1 | 11/2003 | Brenner | 435/6 |
| 6,783,943 B2 | 8/2004 | Christian | 435/6 |
| 6,787,308 B2 | 9/2004 | Balasubramanian | 435/6 |
| 6,812,005 B2 | 11/2004 | Fan | 435/91.2 |
| 6,828,100 B1 | 12/2004 | Ronaghi | 435/6 |
| 6,833,246 B2 | 12/2004 | Balasubramanian | 435/6 |
| 6,864,052 B1 | 3/2005 | Drmanac | 435/6 |
| 6,890,741 B2 | 5/2005 | Fan | 435/91.2 |
| 6,913,884 B2 | 7/2005 | Stuelpnagel | 435/6 |
| 6,977,153 B2 | 12/2005 | Kumar | 435/6 |
| 6,998,228 B2 | 2/2006 | Henderson | 435/4 |
| 7,011,945 B2 | 3/2006 | Qiao | 435/6 |
| 7,064,197 B1 | 6/2006 | Rabbani | 536/24.3 |
| 7,244,559 B2 | 7/2007 | Rothberg | 435/6 |
| 7,264,929 B2 | 9/2007 | Rothberg | 435/6 |
| 7,276,720 B2 | 10/2007 | Ulmer | 356/246 |
| 7,384,737 B2 | 6/2008 | Barnes | 435/6 |
| 7,544,473 B2 | 6/2009 | Brennar | 435/6 |
| 2002/0004204 A1 | 1/2002 | O'Keefe | 435/6 |
| 2002/0055100 A1 | 5/2002 | Kawashima | 435/6 |
| 2002/0076716 A1 | 6/2002 | Sabanayagam | 435/6 |
| 2002/0197621 A1 | 12/2002 | Drmanac | 435/6 |
| 2003/0068629 A1 | 4/2003 | Rothberg | 435/6 |
| 2004/0002090 A1 | 1/2004 | Mayer | 435/6 |
| 2004/0229221 A1 | 11/2004 | Schon | 435/6 |
| 2004/0248144 A1 | 12/2004 | Mir | 435/6 |
| 2004/0248161 A1 | 12/2004 | Rothberg | 435/6 |
| 2005/0019776 A1 | 1/2005 | Callow | 435/6 |
| 2005/0032104 A1 | 2/2005 | Makarov | 453/6 |
| 2005/0037356 A1 | 2/2005 | Gullberg | 435/6 |
| 2005/0042649 A1 | 2/2005 | Balasubramanian | 435/6 |
| 2005/0100939 A1 | 5/2005 | Namsaraev | 435/6 |
| 2005/0191656 A1 | 9/2005 | Drmanac | 435/6 |
| 2005/0214840 A1 | 9/2005 | Chen | 435/6 |
| 2005/0244863 A1 | 11/2005 | Mir | 435/6 |
| 2006/0012793 A1 | 1/2006 | Harris | 356/436 |
| 2006/0024681 A1 | 2/2006 | Smith | 435/6 |
| 2006/0024711 A1 | 2/2006 | Lapidus | 435/6 |
| 2006/0223097 A1 | 10/2006 | Sapolosky | 435/6 |
| 2007/0015182 A1 | 1/2007 | Abarzua | 435/6 |
| 2007/0037152 A1 | 2/2007 | Drmanac | 435/6 |
| 2007/0037197 A1 | 2/2007 | Young | 435/6 |
| 2007/0072208 A1 | 3/2007 | Drmanac | 435/6 |
| 2007/0099208 A1 | 5/2007 | Drmanac | 435/6 |
| 2008/0234136 A1 | 9/2008 | Drmanac | 506/3 |
| 2008/0318796 A1 | 12/2008 | Drmanac | 506/3 |
| 2009/0005252 A1 | 1/2009 | Drmanac | 506/3 |
| 2009/0005259 A1 | 1/2009 | Drmanac | 506/3 |
| 2009/0011416 A1 | 1/2009 | Drmanac | 435/6 |
| 2009/0011943 A1 | 1/2009 | Drmanac | 506/4 |
| 2009/0036316 A1 | 2/2009 | Drmanac | 506/4 |
| 2009/0075343 A1* | 3/2009 | Sparks et al. | 435/91.2 |
| 2009/0099041 A1 | 4/2009 | Church | 506/26 |
| 2009/0118488 A1 | 5/2009 | Drmanac | 536/24.2 |
| 2009/0137404 A1 | 5/2009 | Drmanac | 506/3 |
| 2009/0137414 A1 | 5/2009 | Drmanac | 506/9 |
| 2009/0155781 A1 | 6/2009 | Drmanac | 435/6 |
| 2009/0176652 A1* | 7/2009 | Dahl et al. | 506/7 |
| 2009/0264299 A1 | 10/2009 | Drmanac | 506/3 |

FOREIGN PATENT DOCUMENTS

| | | |
|---|---|---|
| WO | WO 2005/078130 | 8/2005 |
| WO | WO 2005/080605 | 9/2005 |
| WO | WO 2005/082098 | 9/2005 |
| WO | WO 2005/093094 | 10/2005 |
| WO | WO 2005/116262 | 12/2005 |
| WO | WO 2006/007207 | 1/2006 |
| WO | WO 2006/040549 | 4/2006 |
| WO | WO 2006/055521 | 5/2006 |
| WO | WO 2006/073504 | 7/2006 |
| WO | WO 2006/084132 | 8/2006 |
| WO | WO 2006/138257 | 12/2006 |
| WO | WO 2007/014397 | 2/2007 |
| WO | WO 2007/025124 | 3/2007 |
| WO | WO 2007/061425 | 5/2007 |
| WO | WO 2007/062160 | 5/2007 |
| WO | WO 2007/106509 | 9/2007 |
| WO | WO 2007/120208 | 10/2007 |
| WO | WO 2007/121489 | 10/2007 |

OTHER PUBLICATIONS

Callow, Matthew J., et al., "Single Base, Site-Directed Mutagenesis of a 90 Kilobase-Pair P1 Clone," Nucleic Acids Research, v. 22, No. 20, p. 4348-4349, 1994.

Chen et al., "A Homogeneous, Ligase-Mediated DNA Diagnostic Test", Genome Research, vol. 8, No. 5, May 1998, pp. 549-556.

Collins et al, "Directional cloning of DNA fragments at a large distance from an initial probe: A circularization method," Proc. Natl. Acad. Sci., 81: 6812-6816 (1984).

Cowie et al, "Identification of APC gene mutations in colorectal cancer using universal microarray-based combinatorial sequencing-by-hybridization," Human Mutation, 24:261-271 (2004).

Dahl et al, "Multiplex amplification enabled by selective circularization of large sets of genomic DNA fragments," Nucleic Acids Research, 33(8): e71 (2005).

Ladner, D.P. et al., "Multiplex detection of hotspot mutations by rolling circl-enabled universal microarrays," Laboratory Investigation, US and CA Academy of Pa;thology, vol. 81, No. 8, p. 1079-1086 (Aug. 1, 2001).

Li, M. et al., "BEAMing up for detection and quantification of rare sequence variants," Nature Methods, vol. 3, pp. 95-97 (2006).

Metzker, "Emerging Technologies in DNA Sequencing," Genome Research, 15: 1767-1776 (2005).

Shendure et al, "Accurate multiplex polony sequencing of an evolved bacterial genome," Science, 309: 1728-1732 (2005).

Shendure et al, "Advanced Sequencing Technologies: Methods and Goals," Nature Reviews Genetics, vol. 5, pp. 335-344 (2004).

Smirnov et al, "Method of manufacturing whole-genome microarrays by rolling circle amplification," Genes, Chromosomes & Cancer, 40: 72-77 (2004).

Tringe et al, "Metagenomics: DNA Sequencing of Environmental Samples," Nature Reviews Genetics, vol. 6, pp. 805-814 (2005.

Vingron et al., "Sequence Alignment and Penalty Choice Review of Concepts, Case Studies and Implications," J. Mol. Biol, vol. 235, issue 1, pp. 1-12 (1994).

Voss, H. et al., "Efficient Low Redundancy Large-Scale DNA Sequencing at EMBL," J. of Biotechn., v. 41, No. 2, (1995).

* cited by examiner

Schematic of adaptor 700

Schematic of 5' adaptor arm 710

(SEQ ID NO. 3)
(SEQ ID NO. 4)

Schematic of 3' adaptor arm 720

(SEQ ID NO. 5)
(SEQ ID NO. 6)

Schematic of final adaptor 730

```
413333331              2               2         133333314
AACTGCTGANNNNNNNNNNGNNNNNNNNNNCNNNNNNNNNNNACAGCAGAT (SEQ ID NO. 7)
AACTGCTGACGCTTACGATGCACGATACGTCTACGATGCGAACAGCAGA   (SEQ ID NO. 8)
   TGACGACTGCGAATGCTACGTGCTATGCAGATGCTACGCTTGTCGTCTA (SEQ ID NO. 9)
```

METHODS AND OLIGONUCLEOTIDE DESIGNS FOR INSERTION OF MULTIPLE ADAPTORS EMPLOYING SELECTIVE METHYLATION

CROSS REFERENCE TO RELATED APPLICATIONS

This application claims the benefit of priority to U.S. Provisional Patent Application No. 60/985,441, filed Nov. 5, 2007, each of which is hereby incorporated by reference in its entirety.

BACKGROUND

Large-scale sequence analysis of genomic DNA is central to understanding a wide range of biological phenomena related to health and disease in humans and in economically important plants and animals. The need for low-cost, high-throughput sequencing and re-sequencing has led to the development of new approaches to sequencing that employ parallel analysis of many target DNA fragments simultaneously. Improvements to sequencing methods and increasing the amount and quality of data from such methods is of great value in the art.

SUMMARY

Embodiments described and claimed herein address the foregoing and other situations by providing methods to provide repeated cycles of nucleic acid cleavage and ligation to insert multiple DNA adaptors into a population of circular target DNAs at defined positions with respect to one another. The resulting multi-adaptor constructs are then used in massively-parallel nucleic acid sequencing techniques. The technology provided allows for use of the same restriction endonuclease recognition site (e.g., a site for a same Type IIS enzyme) to be used in all adaptors, if desired. The methods presented allow for protection of restriction endonuclease recognition sites both in the adapters and in the target nucleic acid to be sequenced, which avoids excision of certain sequences near or obtaining only limited sequence representation around such restriction endonuclease recognition sites. In addition, the methods presented allow for consecutive insertion of adaptors using the previously-inserted adaptor as a stepping stone for the next.

The described technology provides in one aspect a method for positioning two adaptors with respect to one another in nucleic acid library constructs comprising: obtaining target nucleic acids containing restriction endonuclease recognition sites; ligating a first arm and a second arm of a first adaptor to the target nucleic acids to produce first library constructs, wherein one or both of the first and second adaptor arms comprises a restriction endonuclease recognition site for an enzyme that binds in the adaptor but cleaves in the target nucleic acid; amplifying the first library constructs; creating single-stranded regions in the first and second adaptor arms at the restriction endonuclease recognition site; methylating restriction endonuclease recognition sites in the library constructs; digesting the library constructs with a restriction endonuclease that recognizes the restriction endonuclease recognition sites in the first adaptor; and ligating a second adaptor to the library constructs to produce second library constructs.

The described technology provides in another aspect a method for positioning two adaptors with respect to one another in nucleic acid library constructs comprising: obtaining target nucleic acids containing restriction endonuclease recognition sites; ligating a first arm and a second arm of a first adaptor to the target nucleic acids to produce first library constructs, wherein one or both of the first and second adaptor arms comprises a restriction endonuclease recognition site for an enzyme that binds in the adaptor but cleaves in the target nucleic acid; amplifying the first library constructs; creating single-stranded regions in the first and second adaptor arms at the restriction endonuclease recognition site; methylating restriction endonuclease recognition sites in the library constructs; circularizing and ligating the library constructs; digesting the library constructs with a restriction endonuclease that recognizes the restriction endonuclease recognition sites in the first adaptor; and ligating a second adaptor to the library constructs to produce second library constructs.

The described technology provides in yet another aspect a method for positioning two adaptors with respect to one another in nucleic acid library constructs comprising: obtaining target nucleic acids containing restriction endonuclease recognition sites; ligating a first arm and a second arm of a first adaptor to the target nucleic acids to produce first library constructs, wherein the first and second adaptor arms each comprise part of a restriction endonuclease recognition site for an enzyme that binds in the adaptor but cleaves in the target nucleic acid; amplifying the first library constructs; creating single-stranded regions in the first and second adaptor arms at the restriction endonuclease recognition site; methylating restriction endonuclease recognition sites in the library constructs; circularizing and ligating the library constructs to reconstitute the restriction endonuclease recognition site in the first adaptor; digesting the library constructs with a restriction endonuclease that recognizes the restriction endonuclease recognition sites in the first adaptor; and ligating a second adaptor to the library constructs to produce second library constructs.

Additional aspects of the technology provide methods for positioning two or more adaptors with respect to one another in nucleic acid library constructs comprising: (a) obtaining target nucleic acids containing restriction endonuclease recognition sites; (b) ligating a first arm and a second arm of a first adaptor to the target nucleic acids to produce first library constructs, wherein one or both of the first and second adaptor arms comprises a restriction endonuclease recognition site for an enzyme that binds in the adaptor but cleaves in the target nucleic acid; or the first and second adaptor arms each comprise part of a restriction endonuclease recognition site; (c) amplifying the first library constructs; (d) creating single-stranded regions in the first and second adaptor arms at the restriction endonuclease recognition site; (e) methylating restriction endonuclease recognition sites in the library constructs; (f) digesting the library constructs with a restriction endonuclease that recognizes the restriction endonuclease recognition site in the first adaptor; and (g) repeating processes (b) through (f) until a desired number of adaptors have been inserted into the library constructs, wherein the amplification step is performed using primers complementary to the first and second adaptor arms of each successively-added adaptors.

Additional aspects of the technology provide methods for positioning two or more adaptors with respect to one another in nucleic acid library constructs comprising: (a) obtaining target nucleic acids containing restriction endonuclease recognition sites; (b) ligating a first arm and a second arm of a first adaptor to the target nucleic acids to produce first library constructs, wherein one or both of the first and second adaptor arms comprises a restriction endonuclease recognition site for an enzyme that binds in the adaptor but cleaves in the target nucleic acid; or the first and second adaptor arms each comprise part of a restriction endonuclease recognition site; (c) amplifying the first library constructs; (d) creating single-stranded regions in the first and second adaptor arms at the restriction endonuclease recognition site; (e) methylating restriction endonuclease recognition sites in the library constructs; (f) circularizing and ligating the library constructs; (g) digesting the library constructs with a restriction endonuclease that recognizes the restriction endonuclease recognition site in the first adaptor; and (h) repeating processes (b) through (g) until a desired number of adaptors have been inserted into the library constructs, wherein the amplification step is performed using primers complementary to the first and second adaptor arms of each successively-added adaptors.

Yet other aspects of the technology provide methods for positioning two or more adaptors with respect to one another in nucleic acid library constructs comprising: (a) obtaining target nucleic acids containing restriction endonuclease recognition sites; (b) ligating a first arm and a second arm of a first adaptor to the target nucleic acids to produce first library constructs, the first and second adaptor arms each comprise part of a restriction endonuclease recognition site for an enzyme that binds in the adaptor but cleaves in the target nucleic acid; (c) amplifying the first library constructs; (d) creating single-stranded regions in the first and second adaptor arms at the restriction endonuclease recognition site; (e) methylating restriction endonuclease recognition sites in the library constructs; (f) circularizing and ligating the library constructs to reconstitute the restriction endonuclease recognition site in the first adaptor; (g) digesting the library constructs with a restriction endonuclease that recognizes the restriction endonuclease recognition site in the first adaptor; and (h) repeating processes (b) through (g) until a desired number of adaptors have been inserted into the library constructs, wherein the amplification step is performed using primers complementary to the first and second adaptor arms of each successively-added adaptors.

In some aspects, the restriction endonuclease is a Type IIs restriction endonuclease. In other aspects, the first adaptor has more than one Type IIs restriction endonuclease recognition site. In some aspects, three or more adaptors are added to each library construct. In other aspects, four or more adaptors are added to each library construct. In even other aspects, six or more or eight or more adaptors are added to each library construct. In some aspects, the amplification is performed with uracil-containing primers and the single-stranded regions are created by degradation with uracil-DNA glycosylase enzyme. In other aspects of the method, 5' or 3' exonucleases may be used in a limited digest to create the single-stranded Type IIs restriction endonuclease recognition site regions. Also, in some aspects, ligation of the second and subsequently-added adaptors is performed in an orientation-specific manner through, e.g., nick translation-type methods.

Yet other aspects of the technology provide methods for positioning two adaptors with respect to one another in nucleic acid library constructs comprising: obtaining target nucleic acids containing restriction endonuclease recognition sites; ligating a first adaptor to the target nucleic acids to produce first library constructs, wherein the first adaptor comprises a restriction endonuclease recognition site for an enzyme that binds in the adaptor but cleaves in the target nucleic acid; circularizing the first library constructs; subjecting the first library constructs to circle dependent amplification; blocking one or more methylase sites in the restriction endonuclease recognition site in the first library constructs with a methylase block; methylating restriction endonuclease recognition sites in the target nucleic acids; releasing the methylase block; digesting the first library constructs with a restriction endonuclease that recognizes the restriction endonuclease recognition sites in the first adaptor; and ligating a second adaptor to the first library constructs to produce second library constructs. In some aspects, the restriction endonuclease is a Type IIs restriction endonuclease. In other aspects, the first adaptor has more than one Type IIs restriction endonuclease recognition site. Also, in some aspects, the methylase blocker is a zinc finger, a sequence of PNAs or LNAs, or a triplex-forming oligonucleotide. In other aspects, ligation of the second adaptor is performed such that orientation of the second adaptor relative to the first in the library construct is pre-determined, through, e.g., a nick translation-type protocol.

Additional aspects of the technology provide methods for positioning two or more adaptors with respect to one another in nucleic acid library constructs comprising: (a) obtaining target nucleic acids containing restriction endonuclease recognition sites; (b) ligating a first adaptor to the target nucleic acids to produce first library constructs, wherein the first adaptor comprises a restriction endonuclease recognition site; (c) circularizing the first library constructs; (d) subjecting the first library constructs to circle dependent amplification; (e) blocking one or more methylase sites in the restriction endonuclease recognition site in the first library constructs with a methylase block; (f) methylating restriction endonuclease recognition sites in the target nucleic acids; (g) releasing the methylase block; (h) digesting the first library constructs with a restriction endonuclease that recognizes the restriction endonuclease recognition sites in the first adaptor; (i) repeating processes (b) through (h) until a desired number of adaptors have been inserted into the nucleic acid library constructs, wherein the blocking step is performed with each successively-added adaptor. In some aspects, the restriction endonuclease is a Type IIs restriction endonuclease. In other aspects, the first adaptor has more than one Type IIs restriction endonuclease recognition site. Also, in some aspects, the methylase blocker is a zinc finger, a sequence of PNAs or LNAs, or a triplex-forming oligonucleotide. In some aspects, three or more adaptors are added to each library construct. In other aspects, four or more adaptors are added to each library construct. In even other aspects, six, eight, ten or more adaptors are added to each library construct. In other aspects, ligation of the second and other subsequently-added adaptors is performed such that orientation of the second adaptor relative to the first in the library construct is pre-determined, through, e.g., a nick translation-type protocol.

Also in some aspects, amplicons made by selective methylation of a library construct are provided, as are libraries comprising a multiplicity (five or more) of such amplicons. In other aspects, kits are provided for selecting for desired orientations of multiple adaptors in library constructs employing selective methylation.

In further aspects, the present invention provides methods for selectively activating a recognition site for a Type IIs restriction endonuclease in a nucleic acid sequence. Such methods include the following steps: (a) providing a nucleic acid sequence comprising first and second recognition sites for a Type IIs restriction endonuclease; (b) amplifying the nucleic acid sequence using a uracil-containing primer that has a sequence that is complementary to the first recognition site, thus producing an amplified nucleic acid sequence comprising a first recognition site for a Type IIs restriction endonuclease comprising one or more uracils at or near the first recognition site, and a second recognition site for a Type IIs restriction endonuclease; (c) degrading the one or more uracils at or near the first recognition site, thereby producing a single-stranded region in the first recognition site and protecting the first recognition site from methylation by a methylase that methylates unprotected recognition sites for the Type IIs restriction endonuclease; (f) methylating the second recognition site with the methylase, thus inhibiting digestion of the nucleic acid sequence by the Type IIs restriction endonuclease resulting from recognition of the second recognition site; and (g) making the single-stranded region double-stranded such that the Type IIs restriction endonuclease can recognize the first recognition site and digest the nucleic acid sequence.

In further aspects, the present invention provides methods of positioning a second adaptor with respect to a first adaptor in a nucleic acid template construct. Such methods include the following steps: (a) providing a first linear construct that comprises a target nucleic acid and a first adaptor—this first adaptor itself comprises a first recognition site for a first Type IIs restriction endonuclease; (b) protecting the first recognition site from inactivation; (c) inactivating unprotected restriction endonuclease recognition sites in the first linear construct; (d) circularizing the first linear construct to form a first circular construct; (e) applying the first Type IIs restriction endonuclease to the first circular construct to form a second linear construct, wherein the second linear construct comprises the first adaptor inserted within the target nucleic acid; (f) ligating a second adaptor to the second linear construct to form the nucleic acid template construct, wherein the second adaptor comprises a second recognition site for a second Type IIs restriction endonuclease, thus positioning the second adaptor with respect to the first adaptor in the nucleic acid template construct.

In further aspects, the present invention provides methods of making a library of circular nucleic acid templates each comprising a target nucleic acid sequence and at least two adaptors. Such methods include the following steps: (a) providing fragments of genomic nucleic acid; (b) adding a first arm of a first adaptor to one terminus of a plurality of the fragments; (c) adding a second arm of a first adaptor to the other terminus of a plurality of the fragments to form first linear constructs, wherein the first and second arms of the first adaptor, when ligated, form the first adaptor and produce a first recognition site for a first Type IIs restriction endonuclease; (d) protecting the first recognition site in the first linear constructs from inactivation; (e) inactivating unprotected first recognition sites, if any, present in said first linear constructs; (f) circularizing the first linear constructs by ligating the first and second adaptor arms to form first circular constructs; (g) cleaving the first circular constructs with the first Type IIs restriction endonuclease to form second linear constructs comprising the first adaptor inserted within the target nucleic acid, wherein the first Type IIs restriction endonuclease binds to the protected first recognition site and cleaves at a position in the first circular constructs outside of the first adaptor; (h) adding a first arm of a second adaptor to one terminus of a plurality of the second linear constructs; (i) adding a second arm of a second adaptor to the other terminus of a plurality of the fragments to form second linear constructs, wherein the first and second arms of the second adaptor, when ligated, form the second adaptor and form a second Type IIs recognition site; (j) circularizing the second linear constructs by ligating the first and second adaptor arms of the second adaptor to form second circular constructs, thereby making the library of circular nucleic acid templates.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

BRIEF DESCRIPTIONS OF THE DRAWINGS

DEFINITIONS

Figure 1:
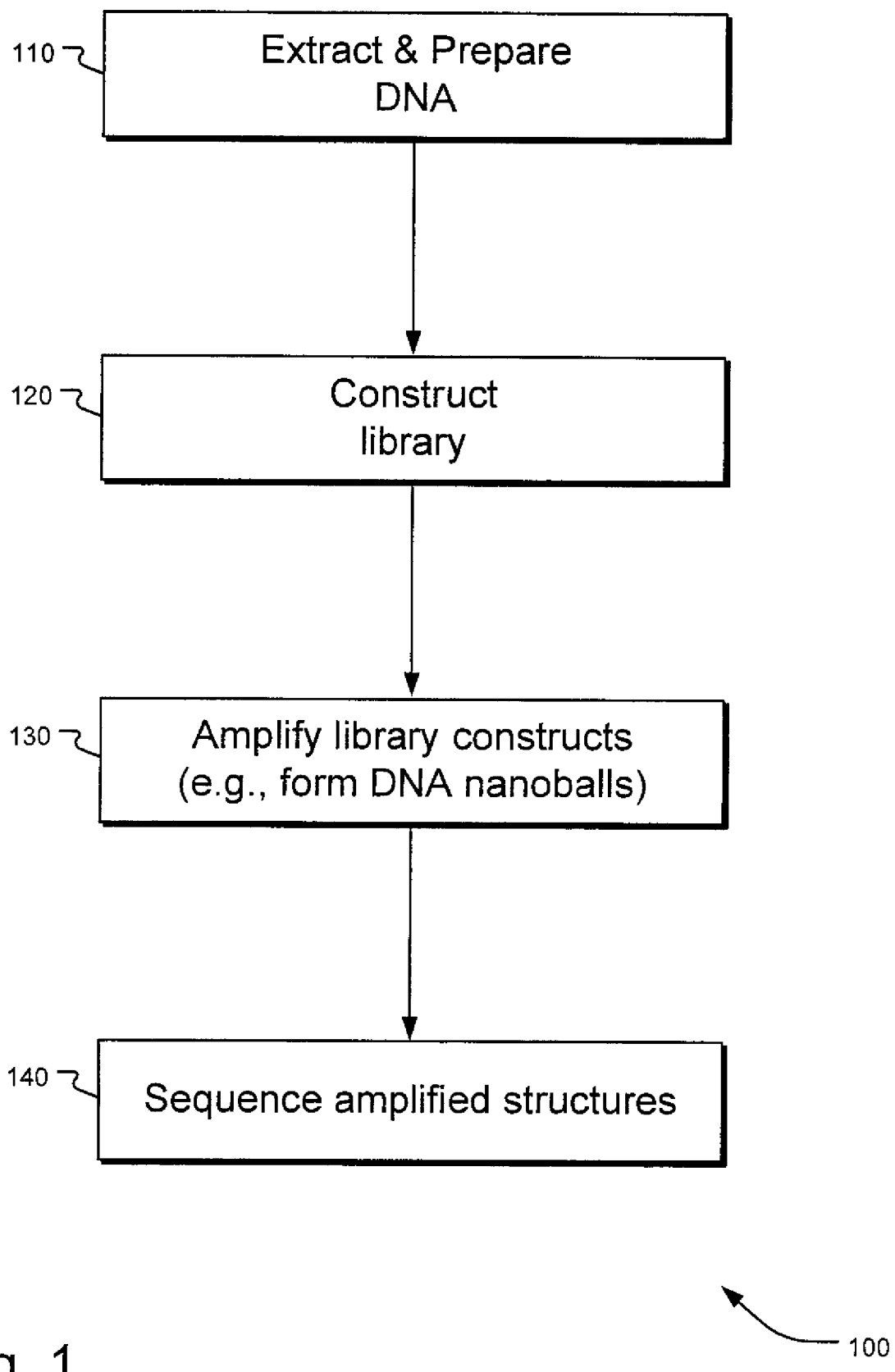
FIG. 1 is a simplified flow diagram of an overall method for sequencing nucleic acids using the processes of the claimed invention.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Diefenbach, Dveksler, Eds. (2003), *PCR Primer: A Laboratory Manual*; Bowtell and Sambrook (2003), DNA Microarrays: *A Molecular Cloning Manual*; Mount (2004), *Bioinformatics:*

*Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, *"Oligonucleotide Synthesis: A Practical Approach"* 1984, IRL Press, London; Nelson and Cox (2000), *Lehninger, Principles of Biochemistry* 3rd Ed., W.H. Freeman Pub., New York, N.Y.; and Berg et al. (2002) *Biochemistry,* 5th Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "an agent" refers to one agent or mixtures of agents, and reference to "the method of administration" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

"Adaptor" refers to an engineered construct comprising "adaptor elements" where one or more adaptors may be interspersed within target nucleic acid in a library construct. The adaptor elements or features included in any adaptor vary widely depending on the use of the adaptors, but typically include sites for restriction endonuclease recognition and/or cutting, sites for primer binding (for amplifying the library constructs) or anchor binding (for sequencing the target nucleic acids in the library constructs), nickase sites, and the like. In some aspects, adaptors are engineered so as to comprise one or more of the following: 1) a length of about 20 to about 250 nucleotides, or about 40 to about 100 oligonucleotides, or less than about 60 nucleotides, or less than about 50 nucleotides; 2) features so as to be ligated to the target nucleic acid as two "arms"; 3) different and distinct anchor binding sites at the 5' and the 3' ends of the adaptor for use in sequencing of adjacent target nucleic acid; and 4) one or more restriction sites.

"Amplicon" means the product of a polynucleotide amplification reaction. That is, it is a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle dependent amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and US Pub. No. 2006/0024711).

"Circle dependant replication" or "CDR" refers to multiple displacement amplification of a double-stranded circular template using one or more primers annealing to the same strand of the circular template to generate products representing only one strand of the template. In CDR, no additional primer binding sites are generated and the amount of product increases only linearly with time. The primer(s) used may be of a random sequence (e.g., one or more random hexamers) or may have a specific sequence to select for amplification of a desired product. Without further modification of the end product, CDR often results in the creation of a linear construct having multiple copies of a strand of the circular template in tandem, i.e. a linear, single-stranded concatamer of multiple copies of a strand of the template.

"Circle dependant amplification" or "CDA" refers to multiple displacement amplification of a double-stranded circular template using primers annealing to both strands of the circular template to generate products representing both strands of the template, resulting in a cascade of multiple-hybridization, primer-extension and strand-displacement events. This leads to an exponential increase in the number of primer binding sites, with a consequent exponential increase in the amount of product generated over time. The primers used may be of a random sequence (e.g., random hexamers) or may have a specific sequence to select for amplification of a desired product. CDA results in a set of concatemeric double-stranded fragments is formed.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Duplex" means at least two oligonucleotides or polynucleotides that are fully or partially complementary and which undergo Watson-Crick type base pairing among all or most of their nucleotides so that a stable complex is formed. The terms "annealing" and "hybridization" are used interchangeably to mean formation of a stable duplex. "Perfectly matched" in reference to a duplex means that the poly- or oligonucleotide strands making up the duplex form a double-stranded structure with one another such that every nucleotide in each strand undergoes Watson-Crick base pairing with a nucleotide in the other strand. A "mismatch" in a duplex between two oligonucleotides or polynucleotides means that a pair of nucleotides in the duplex fails to undergo Watson-Crick basepairing.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of less than about 1 M, more usually less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of 30° C. are suitable for allele-specific probe hybridizations.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921.

"Methylases" or "methyltransferases" are enzymes of sub-subclass EC 2.1.1, which transfer a methyl group from S-adenosylmethionine to either adenine or cytosine residues. A "sequence-specific methylase" is a methylase that catalyzes the transfer of a methyl group to one or more nucleotide bases in a nucleic acid sequence upon recognition of one or more sequences of nucleotides in the nucleic acid sequence. Exemplary methylases include the dam, AluI, BamHI, EcoRI, HaeIII, HhaI, HpaII, MspI, TaqI, and CpG (M.SssI) Methylases. A "methylase blocker" may be a DNA binding protein or other DNA binding entity, or a chemical composition or physical configuration that prevents binding of a methylase to a nucleic acid sequence, or otherwise prevents methylation of a nucleic acid sequence.

"Microarray" or "array" refers to a solid phase support having a surface, preferably but not exclusively a planar or substantially planar surface, which carries an array of sites containing nucleic acids such that each site of the array comprises identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed. (2000), *Microarrays: A Practical Approach* (IRL Press, Oxford). As used herein, "random array" or "random microarray" refers to a microarray where the identity of the oligonucleotides or polynucleotides is not discernable, at least initially, from their location but may be determined by a particular operation on the array, such as by sequencing, hybridizing decoding probes or the like. See, e.g., U.S. Pat. Nos. 6,396,995; 6,544,732; 6,401,267; and 7,070,927; WO publications WO 2006/073504 and 2005/082098; and US Pub Nos. 2007/0207482 and 2007/0087362.

"Nucleic acid", "oligonucleotide", "polynucleotide", "oligo" or grammatical equivalents used herein refer generally to at least two nucleotides covalently linked together. A nucleic acid generally will contain phosphodiester bonds, although in some cases nucleic acid analogs may be included that have alternative backbones such as phosphoramidite, phosphorodithioate, or methylphosphoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Probe" means generally an oligonucleotide that is complementary to an oligonucleotide or target nucleic acid under investigation. Probes used in certain aspects of the claimed invention are labeled in a way that permits detection, e.g., with a fluorescent or other optically-discernable tag.

"Sequence determination" in reference to a target nucleic acid means determination of information relating to the sequence of nucleotides in the target nucleic acid. Such information may include the identification or determination of partial as well as full sequence information of the target nucleic acid. The sequence information may be determined with varying degrees of statistical reliability or confidence. In one aspect, the term includes the determination of the identity and ordering of a plurality of contiguous nucleotides in a target nucleic acid starting from different nucleotides in the target nucleic acid.

"Target nucleic acid" means a nucleic acid from a gene, a regulatory element, genomic DNA, cDNA, RNAs including mRNAs, rRNAs, siRNAs, miRNAs and the like and fragments thereof. A target nucleic acid may be a nucleic acid from a sample, or a secondary target such as a product of an amplification reaction.

As used herein, the term "$T_m$" is commonly defined as the temperature at which half of the population of double-stranded nucleic acid molecules becomes dissociated into single strands. The equation for calculating the $T_m$ of nucleic acids is well known in the art. As indicated by standard references, a simple estimate of the $T_m$ value may be calculated by the equation: $T_m=81.5\pm16.6(\log 10[Na^+])0.41(\%[G+C])-675/n-1.0$ m, when a nucleic acid is in aqueous solution having cation concentrations of 0.5 M, or less, the (G+C) content is between 30% and 70%, n is the number of bases, and m is the percentage of base pair mismatches (see e.g., Sambrook J et al. (2001), Molecular Cloning, A Laboratory Manual, 3rd Ed., (Cold Spring Harbor Laboratory Press)). Other references include more sophisticated computations, which take structural as well as sequence characteristics into account for the calculation of $T_m$ (see also, Anderson and Young (1985), "Quantitative Filter Hybridization", *Nucleic Acid Hybridization*, and Allawi and SantaLucia (1997), Biochemistry 36:10581-94).

DETAILED DESCRIPTION

Technology is described herein for providing nucleic acid constructs having interspersed adaptors inserted in a desired position with respect to one another for use in large-scale sequencing methods. The technology provided allows for use of the same restriction endonuclease recognition site (for an enzyme that cleaves outside its recognition site) to be used in all adaptors and amplification of the nucleic acid after incorporation of an adapter and before restriction, if desired. For example, the same Type IIs restriction endonuclease recognition site may be used in the first adaptor added to the library construct, the site in the first adaptor inactivated, the second adaptor added to the library construct, the sites in both adaptors inactivated, the third adaptor added to the library construct, and so on. In addition, the methods provide library constructs where the restriction recognition site is positioned very close to one end of the adapter; i.e., close to the target nucleic acid. Moreover, the methods presented allow for protection of the restriction endonuclease recognition sites in the target nucleic acid, which avoids excision of certain sequences near or obtaining only limited sequence representation around such Type IIs restriction endonuclease recognition sites. In addition, the methods presented allow for consecutive insertion of adaptors using the previously-inserted adaptor as a stepping stone for the next.

Methods presented allow for protecting genomic or other nucleic acid restriction sites from being recognized by a restriction endonuclease, and generating circular DNA with multiple insertions of adaptors using only one restriction endonuclease. In preferred embodiments, Type IIs restriction endonucleases are employed. In one aspect, sequence-specific methylases are used that have the same recognition site as the Type IIs restriction endonuclease being used. By employing this combination of sequence-specific methylases and Type IIs restriction endonucleases, all Type IIs restriction endonuclease recognition sites in the target nucleic acid as well as the Type IIs restriction endonuclease recognition sites in any previously-inserted adaptor can be protected from digestion (assuming, of course, the Type IIs restriction endonuclease is methylation sensitive). However, because the library construct preparation process requires active Type IIs restriction endonuclease recognition sites in the most recently-added adaptor, the Type IIs restriction endonuclease recognition sites in the most recently-added adaptor must be protected from methylation. In one aspect of a methylation protection procedure, library constructs are methylated before the new adapter or adapter arms is/are ligated to these library constructs; however, this approach does not allow for amplification of the library constructs before using the restriction enzyme binding sites in the new adapter because all previous methyl groups will be also removed. In other aspects, the new adaptor or adaptor arms is/are ligated to the library constructs before methylation allowing for amplification of the library constructs after ligation but before methylation.

In one methylation protection procedure, the most recently-added adaptor's Type IIs restriction endonuclease recognition site is activated only upon circularization. In short, nucleic acid is fragmented, with some fragments containing Type IIs restriction endonuclease recognition sites native to the target nucleic acid that desirably will be protected from digestion. First, the first and second arms of a first adaptor, each containing portions of a Type IIs restriction endonuclease recognition site or one arm containing the entire site, are ligated to the fragmented nucleic acid. Next, PCR is performed using uracil-modified primers complementary to the first and second arms of the first adaptor. The primers generate a PCR product with uracils close to the Type IIs restriction endonuclease recognition site in the first and second arms of the first adaptor such that, when the uracils are degraded, the PCR product becomes single-stranded in the Type IIs restriction endonuclease recognition site. In this preferred method, the restriction site is completely single-stranded after U degradation. A linker complementary to the adaptor at the restriction recognition site, with, e.g., a T-tail, is used in the ligation reaction after the methylation reaction to form the circle and create double-stranded nucleic acid at the restriction site.

In some aspects of this procedure, the linker is not phosphorylated, providing a "nick" in the circle that can be used to initiate CDR, CDA or nick translation or to select the DNA strand without a nick. In some aspects, the linker may have one or more Uracil bases to open a nick for nick translation after IIS restriction enzyme cleavage (as described in detail, infra).

In an alternative aspect of this invention, controlled or limited digestion using 5' or 3' exonucleases may be used after the amplification step to create the single-stranded regions in the Type IIs restriction endonuclease recognition sites, which then may be repaired or refilled using a polymerase and, e.g., dNTPs. After the single-stranded gap is filled, ligase is used to form a circle. Using 5' exonuclease allows for short adapters (15-25 bases) to be used and positioning of the restriction site at the very end of the adapter. Controlled 3' exonuclease digests (e.g., controlling digestion time, concentration, buffer conditions alone or in combination) may also be used to form single-stranded nucleic acid regions after the amplification step. When employing a 3' exonuclease digest, the adapter arms do not need to have complementary sequences. After filling in the single-stranded region by polymerase, regular or blunt-end ligation may be performed to circularize the library constructs (blunt-end ligation is used if the adaptor arms are not complementary). Other techniques can be used to render the restriction endonuclease recognition sites single-stranded as well.

Once the region(s) of the adaptor at the restriction endonuclease recognition site are rendered single-stranded, a sequence-specific methylase that recognizes only double-stranded Type IIs restriction endonuclease recognition sites is used to protect the double-stranded Type IIs restriction endonuclease recognition sites in the target nucleic acid. Circularization of the library constructs (adaptors+target nucleic acid) is then performed. In some aspects, the single-stranded Type IIs restriction endonuclease recognition site portions in the first and second arms of the first adaptor ligate to reconstitute a double-stranded Type IIs restriction endonuclease recognition site in the first adaptor. In other aspects, reconstitution is not necessary as either the first adaptor arm, the second adaptor arm or both comprise an intact restriction endonuclease recognition site. Next, the library constructs are digested with a Type IIs restriction endonuclease that will cut only the non-methylated double-stranded Type IIs restriction endonuclease recognition site in the first adaptor. The process is then repeated. When the next round of methylation is carried out, the double-stranded Type IIs restriction endonuclease recognition sites in any previously-inserted adaptor(s) are protected from cleavage at the endonuclease recognition site.

Another method presented is a methylation protection procedure based on using methylation blockers (e.g., zinc finger binding proteins), other nucleic acid binding entities, chemical compositions or physical configurations of the nucleic acid that prevents the binding of a methylase to a nucleic acid sequence, or other methods that prevent methylation of a nucleic acid sequence. For example, by designing adaptors to have sequence-specific zinc binding regions surrounding or partially overlapping the Type IIs restriction endonuclease recognition site in each adaptor, the Type IIs restriction endonuclease recognition sites of each adaptor can be selectively protected from methylation.

A great deal of progress has been made in the development of modular protein domains that recognize specific triplets of nucleic acid sequence and bind to a chosen, specified sequence. The $Cys_2$-$His_2$ zinc finger motif is a useful structural scaffold on which sequence-specific proteins can be constructed. A single zinc finger domain consists of approximately thirty amino acids with a simple ββα fold stabilized by hydrophobic interactions and the chelation of a single zinc ion. Presentation of the α-helix of this domain into the major groove of DNA allows for sequence-specific base contacts. Each zinc finger domain typically recognizes three base pairs of nucleic acid, though variation in helical presentation can allow for recognition of a more extended site. In contrast to other nucleic acid binding proteins that rely on dimerization of protein domains for extending protein-nucleic acid contacts to longer nucleic acid sequences, simple covalent tandem repeats of the zinc finger domain allow for the recognition of longer asymmetric sequences of nucleic acid. Parameters to take into consideration when designing appropriate zinc finger proteins include specificity and affinity. Production of zinc finger proteins can be best achieved using either of two methods. The first is to assemble the fingers sequentially using standard techniques. For a six-finger protein recognizing an 18 bp site, cloning can be performed in about two weeks or less, especially if the two 3-finger subsites are cloned in parallel and assembled in the final step. Alternatively, an efficient method for obtaining the final nucleic acid sequence is to have it commercially synthesized.

In another aspect of the claimed methods, peptide nucleic acids (PNAs) or locked nucleic acids (LNAs) are used to protect specific sequences from methylation. PNAs and LNAs bind more strongly to complementary DNA and can protect specific sequences from enzymatic digestion (see, e.g., Nielsen, et al. (1993) *Nucleic Acids Research* 21(2):197-200). By designing the adaptors to have specific sequences surrounding the Type IIs restriction endonuclease recognition site, each adaptor can hybridize to a unique PNA or LNA. Adding a PNA or LNA that corresponds to the most-recently added adaptor will hybridize to the most recently added adaptor, specifically protecting its Type IIs restriction endonuclease recognition site from methylation. In this strand-invasion reaction, the PNA or LNA oligonucleotide invades the double-stranded nucleic acid or the double-stranded nucleic acid is temporarily at least partially denatured to single-stranded form at the binding site. After the PNA or LNA oligonucleotide hybridizes (with high binding energy) to the complementary strand, the native nucleic acid strand is likely displaced and forms a "loop". This structure alone or in combination with PNA/LNA chemistry prevents the methylase from binding to or prevents methylase enzymatic action on this restriction site. In yet another aspect of the claimed invention, triplex-forming oligonucleotides are used to block methylation of the Type IIs restriction endonuclease recognition site. Triplex-forming oligonucleotides have been demonstrated to be sequence-specific, selectively activating or inactivating gene expression in a number of systems (see, e.g., Goni, et al., (2003) *Nucleic Acid Res.* 31:6064-78; Majumdar, et al., (2003 *J. Biol. Chem.* 278:11072-77; Diviacco, et al., (2001) *FASEB J* 15:2660-68 and Knauert and Glazer (2001) *Hum. Mol. Gen.* 10:2243-51).

Overview of Sequencing Approaches for use with the Present Invention

FIG. 1 is a simplified flow diagram of an overall method 100 for sequencing nucleic acids using the processes of the claimed invention. Generally, creation of a target molecule for sequencing is accomplished by extracting and preparing (e.g., fractionating, shearing or cleaving) target nucleic acids 110, constructing a library with the fractionated target nucleic acids using engineered adaptors 120, replicating the library constructs to form amplified library constructs (e.g., forming DNA nanoballs through circle dependent replication) 130, and sequencing the amplified target nucleic acids 140.

In process 110 of method 100, the target nucleic acids for some aspects are derived from genomic DNA. In some aspects such as whole genome sequencing, 10-100 genome-equivalents of DNA are preferably obtained to ensure that the population of target DNA fragments covers the entire genome. The target genomic DNA is isolated using conventional techniques, for example as disclosed in Sambrook and Russell, Molecular Cloning: A Laboratory Manual, cited supra. The target genomic DNA is then fractionated or fragmented to a desired size by conventional techniques including enzymatic digestion, shearing, or sonication. Fragment size of the target nucleic acid can vary depending on the source target nucleic acid and the library construction methods used, but typically range from 50 nucleotides in length to over 11 kb in length, including 200-700 nucleotides in length, 400-600 nucleotides in length, 450-550 in length, or 4 kb to over 10 kb in length. Fragments can be selected for use in methods of the invention described herein that are within a selected range of sizes. It will be appreciated that this range of sizes can be of any range useful for downstream applications such as sequencing applications described herein. In an exemplary embodiment, fragments chosen for use in methods of the invention range from 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length. Fragments of a particular size range (plus or minus 10, 20, 30, 40, 50, 60, 70, 80, 90, 100 or more bases) can be isolated using methods well known in the art, including without limitation gel fractionation. Alternatively, in some aspects, the target nucleic acids comprise mRNAs or cDNAs. In specific embodiments, the target DNA is created using isolated transcripts from a biological sample. Isolated mRNA may be reverse transcribed into cDNAs using conventional techniques, again as described in *GenomeAnalysis: A Laboratory Manual Series* (Vols. I-IV) or *Molecular Cloning: A Laboratory Manual*.

In process 120 of method 100, a library is constructed using the fragmented target nucleic acids. Library construction will be discussed in detail infra; briefly, the library constructs are assembled by inserting adaptor molecules at a multiplicity of sites throughout each target nucleic acid fragment. The interspersed adaptors permit acquisition of sequence information from multiple sites in the target nucleic acid consecutively or simultaneously. In some aspects, the interspersed adaptors are inserted at intervals within a contiguous region of the target nucleic acids at predetermined positions. The intervals may or may not be equal. In some aspects, the accuracy of the spacing between interspersed adaptors may be known only to an accuracy of one to a few nucleotides. In other aspects, the spacing of the adaptors is known, and the orientation of each adaptor relative to other adaptors in the library constructs is known.

In process 130 of method 100, the library constructs are amplified and, in some aspects, are replicated to form DNA nanoballs. In such a process, the library constructs (the target nucleic acids with the interspersed adaptors) are replicated in such a way so as to form single-stranded DNA concatemers of each library construct, each concatamer comprising multiple linear tandem repeats of the library construct. Single-stranded DNA concatemers under conventional conditions (in buffers, e.g., TE, SSC, SSPE or the like) form random coils in a manner known in the art (e.g., see Edvinssom (2002), "On the size and shape of polymers and polymer complexes," Dissertation 696 (University of Uppsala)). Concatemeric DNA randomly coiled forms nanoballs (also termed "DNA nanoballs", "nucleic acid nanoballs" or "DNBs").

In process 140 of method 100, the DNBs formed in process 130 are sequenced. In some aspects, the DNBs are randomly arrayed on a planar surface. The DNBs may be covalently or noncovalently attached to the planar surface. The target nucleic acids within each DNB are then sequenced by iterative interrogation using sequencing-by-synthesis techniques and/or sequencing-by-ligation techniques.

Figure 2:
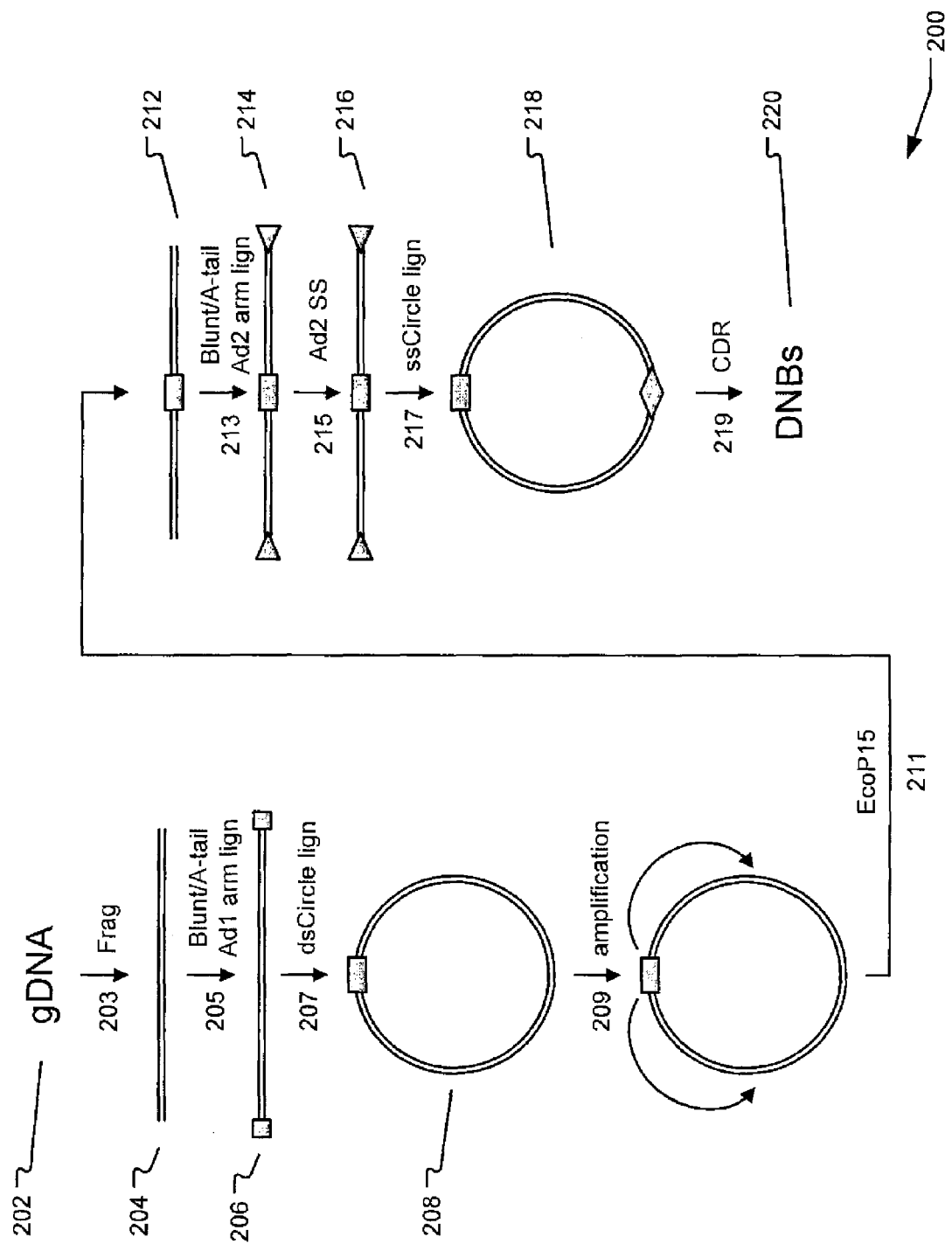
FIG. 2 is a schematic representation of one aspect of a method for assembling adaptor/target nucleic acid library constructs.

FIG. 2 is a schematic representation of one aspect of a method for assembling adaptor/target nucleic acid library constructs. DNA, such as genomic DNA 202, is isolated and fragmented 203 into target nucleic acids 204 using standard techniques as described briefly above. The fragmented target nucleic acids 204 are then repaired so that the 5' and 3' ends of each strand are flush or blunt ended. Following this reaction, each fragment is "A-tailed" with a single A added to the 3' end of each strand of the fragmented target nucleic acids using a non-proofreading polymerase 205. Also as part of process 205, a first and second arm of a first adaptor is then ligated to each target nucleic acid, producing a target nucleic acid with adaptor arms ligated to each end 206. In one aspect, the adaptor arms are "T tailed" to be complementary to the A tailing of the target nucleic acid, facilitating ligation of the adaptor arms in a known orientation. Similarly, G/C tailing can be performed.

In a preferred embodiment, the invention provides adaptor ligation to each fragment in a manner that minimizes the creation of intra- or intermolecular ligation artefacts. This is desirable because random fragments of target nucleic acids forming ligation artefacts with one another create false proximal genomic relationships between target nucleic acid fragments, complicating the sequence alignment process. The aspect shown in FIG. 2 shows step 205 as a combination of blunt end repair and an A tail addition. This preferred aspect using both A tailing and T tailing to attach the adaptor to the DNA fragments prevents random intra- or inter-molecular associations of adaptors and fragments, which reduces artefacts that would be created from self-ligation, adaptor-adaptor or fragment-fragment ligation.

As an alternative to A/T tailing (or G/C tailing), various other methods can be implemented to prevent formation of ligation artefacts of the target nucleic acids and the adaptors, as well as orient the adaptor arms with respect to the target nucleic acids, including using complementary NN overhangs in the target nucleic acids and the adaptor arms, or employing blunt end ligation with an appropriate target nucleic acid to adaptor ratio to optimize single fragment nucleic acid/adaptor arm ligation ratios.

In process 207, the linear target nucleic acid 206 is circularized, a process that will be discussed in detail infra, resulting in a circular library construct 208 comprising target nucleic acid and an adaptor. Note that the circularization process results in bringing the first and second arms of the first adaptor together to form a contiguous adaptor sequence in the circular construct. In process 209, the circular construct is amplified, such as by circle dependent amplification, using, e.g., random hexamers and Φ29 or helicase. Alternatively, target nucleic acid/adaptor structure 206 may remain linear, and amplification may be accomplished by PCR primed from sites in the adaptor arms. The amplification 209 preferably is a controlled amplification process and uses a high fidelity, proof-reading polymerase, resulting in a sequence-accurate library of amplified target nucleic acid/adaptor constructs where there is sufficient representation of the genome or one or more portions of the genome being queried.

In aspects herein, the first adaptor comprises two Type IIs restriction endonuclease recognition sites, positioned such that the target nucleic acid outside the recognition sequence (and outside of the adaptor) is cut 210. The arrows around structure 210 indicate the recognition sites and the site of restriction. In process 211, EcoP15, a Type IIs restriction endonuclease, is used to cut the library constructs. Note that in the aspect shown in FIG. 2, a portion of each library construct mapping to a portion of the target nucleic acid will be cut away from the construct (the portion of the target nucleic acid between the arrow heads in structure 210). Restriction of the library constructs with EcoP15 in process 211 results in a library of linear constructs containing the first adaptor, with the first adaptor "interior" to the ends of the linear construct 212. The resulting linear library construct will have a size defined by the distance between the endonuclease recognition sites and the endonuclease restriction site plus the size of the adaptor. In process 213, the linear construct 212, like the fragmented target nucleic acid 204, is treated by conventional methods to become blunt or flush ended, A tails comprising a single A are added to the 3' ends of the linear library construct using a non-proofreading polymerase and first and second arms of a second adaptor are ligated to ends of the linearized library construct by A-T tailing and ligation 213. Similarly G-C tailing can be performed. The resulting library construct comprises the structure seen at 214, with the first adaptor interior to the ends of the linear construct, with target nucleic acid flanked on one end by the first adaptor, and on the other end by either the first or second arm of the second adaptor.

In process 215, the double-stranded linear library constructs are treated so as to become single-stranded 216, and the single-stranded library constructs 216 are then ligated 217 to form single-stranded circles of target nucleic acid interspersed with two adaptors 218. The ligation/circularization process of 217 is performed under conditions that optimize intramolecular ligation.

Next, in the two-adaptor aspect shown in FIG. 2, the single-stranded, circularized library constructs 218 are amplified by circle dependent replication 219 to form DNA nanoballs 220. Circle dependent replication is performed, e.g., using specific primers where the amplification product displaces its own tail, producing linear, tandem single-stranded copies of ⊢target nucleic acid/adaptor 1/target nucleic acid/adaptor 2⊣ library constructs. As the tandem copies begin to multiply, the library constructs begin to coil and form secondary structures, ultimately forming DNA nanoballs. Each library construct contains in some aspects between about ten to about 5000 copies, or from about 250 copies to about 2500 copies of the ⊢target nucleic acid/adaptor 1/target nucleic acid/adaptor 2→ repeats, and preferably contains about 500 to about 1200 copies of the ⊢target nucleic acid/adaptor 1/target nucleic acid/adaptor 2→ repeats. The resulting DNA nanoballs 220, then, are clonal populations of DNA in discrete structures, which can then be arrayed and sequenced (process not shown).

Figure 3:
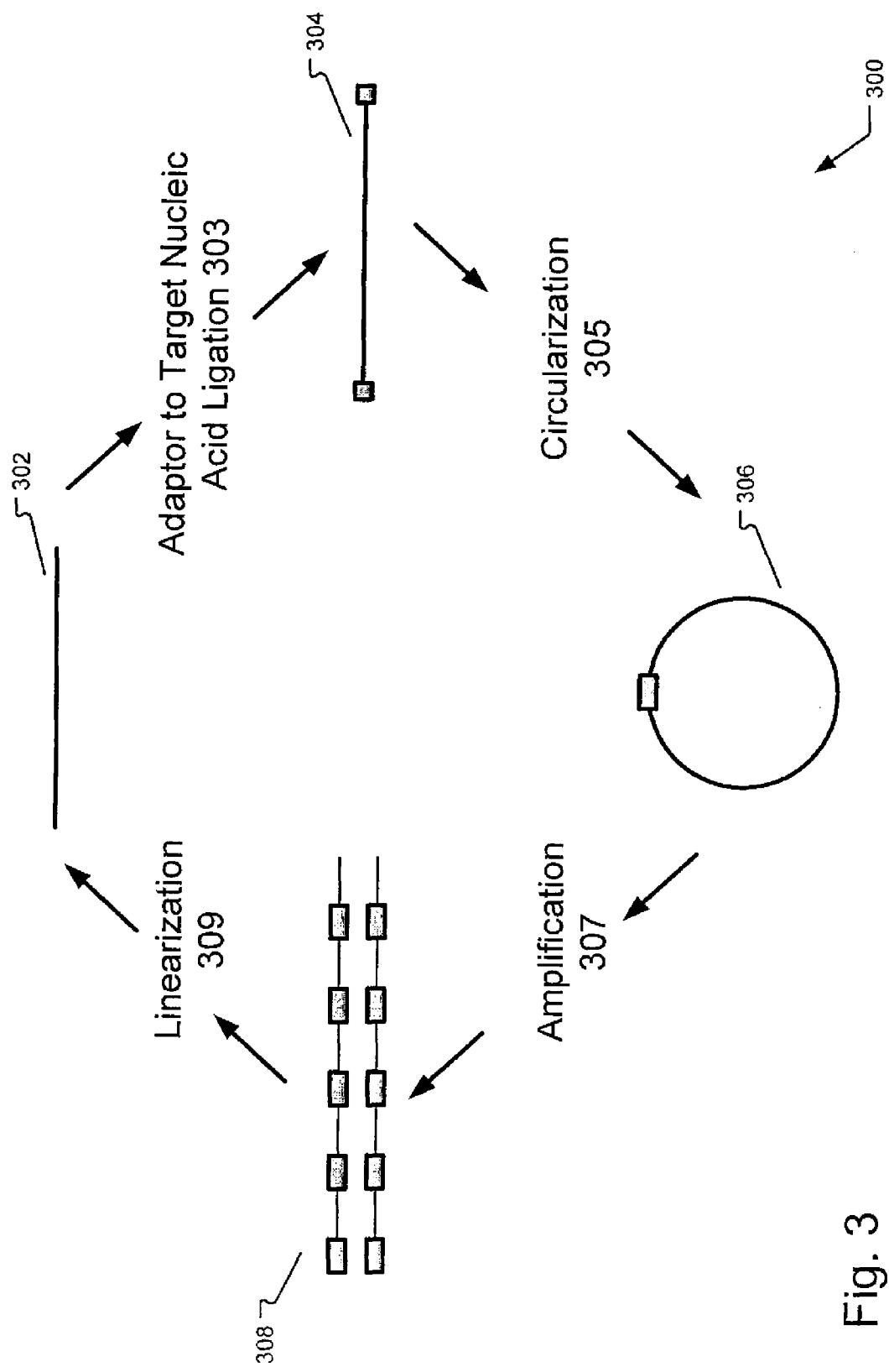
FIG. 3 is a schematic illustration of a basic adaptor insertion process.

FIG. 3 is a simplified schematic illustration showing the cyclical nature of the basic adaptor insertion process 300 where two, three, four, five or more adaptors can be inserted into a target nucleic acid. A fragmented target nucleic acid is shown at 302. Process 303 provides adaptor arm to target nucleic acid ligation (as was described with some detail in the discussion of the aspect shown in FIG. 2), resulting in a linear target nucleic acid with first and second adaptor arms of a first adaptor ligated onto its ends 304. The adaptor arms are then ligated to one another in an intramolecular reaction that results in a circularization of the target nucleic acid/adaptor library construct 306. The library construct is then amplified 307 resulting in a population comprising a plurality of copies of each target nucleic acid/adaptor library construct 308. These library constructs 308 are then cleaved 309 (for example, by restriction with a Type IIs restriction endonuclease recognizing one or more sites in the adaptor and cutting in the target nucleic acid sequence), and the cycle continues to add second, third, fourth or more adaptors.

Figure 4:
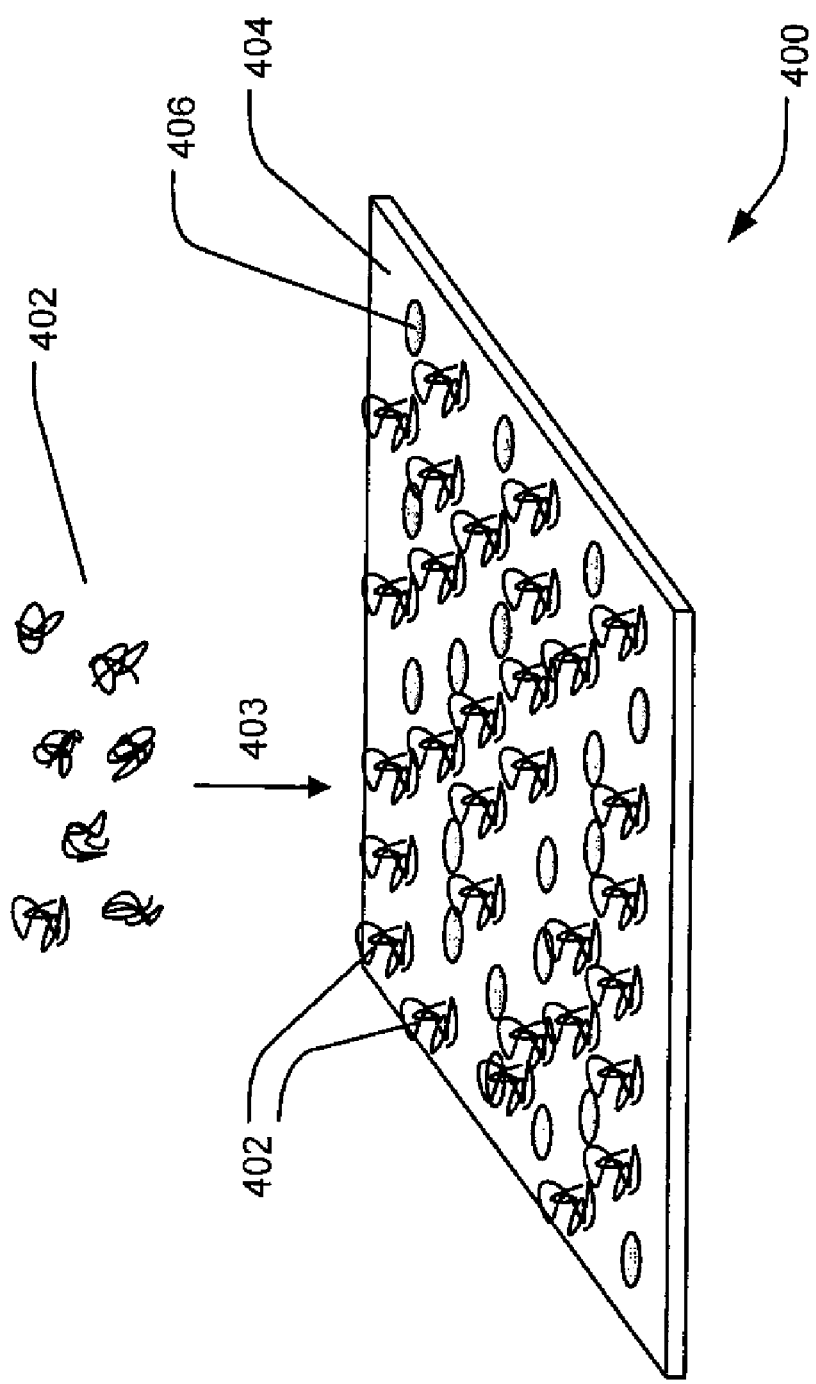
FIG. 4 is a schematic illustration of one aspect of a DNA array employing multi-adaptor nucleic acid library constructs.

FIG. 4 is a schematic illustration of one aspect of a DNA array 400 employing multi-adaptor nucleic acid library constructs. The multi-adaptor nucleic acid library constructs in the form of DNA nanoballs (DNBs) are seen at 402. DNBs are arrayed on a planar matrix 404 having discrete sites 406. The DNBs 402 may be fixed to the discrete sites by a variety of techniques, including covalent attachment and non-covalent attachment. In one embodiment, the surface of the matrix 406 may comprise attached capture oligonucleotides that form complexes, e.g., double-stranded duplexes, with a segment of an adaptor component of the DNB. In other embodiments, capture oligonucleotides may comprise oligonucleotide clamps, or like structures, that form triplexes with adaptor oligonucleotides (see, e.g., U.S. Pat. No. 5,473,060). In another embodiment, the surface of the array matrix 406 may have reactive functionalities that react with complementary functionalities on the DNBs to form a covalent linkage (see, e.g., Beaucage (2001), Current Medicinal Chemistry 8:1213-1244). Once the DNBs are arrayed, the adaptors interspersed in the target nucleic acids are used to acquire sequence information of the target nucleic acids. A variety of sequencing methodologies may be used with multi-adaptor nucleic acid library constructs, including but not limited to hybridization methods as disclosed in U.S. Pat. Nos. 6,864,052; 6,309,824; 6,401,267; sequencing-by-synthesis methods as disclosed in U.S. Pat. Nos. 6,210,891; 6,828,100, 6,833,246; 6,911,345; Margulies, et al. (2005), *Nature* 437:376-380 and Ronaghi, et al. (1996), *Anal. Biochem.* 242:84-89; and ligation-based methods as disclosed in U.S. Pat. No. 6,306,597; and Shendure et al. (2005) *Science* 309:1728-1739, all of which are incorporated by reference in their entirety.

In one aspect, the DNBs described herein—particularly those with inserted and interspersed adapters—are used in sequencing by combinatorial probe-anchor ligation reaction (cPAL) (see U.S. Ser. No. 11/679,124, filed Feb. 24, 2007). In brief, cPAL comprises cycling of the following steps: First, an anchor is hybridized to a first adaptor in the DNBs (typically immediately at the 5' or 3' end of one of the adaptors). Enzymatic ligation reactions are then performed with the anchor to a fully degenerate probe population of, e.g., 8-mer probes that are labeled, e.g., with fluorescent dyes. Probes may comprise, e.g., about 6 to about 20 bases in length, to about 7 to about 12 bases in length. At any given cycle, the population of 8-mer probes that is used is structured such that the identity of one or more of its positions is correlated with the identity of the fluorophore attached to that 8-mer probe. For example, when 7-mer sequencing probes are employed, a set of fluorophore-labeled probes for identifying a base immediately adjacent to an interspersed adaptor may have the following structure: 3'-F1-NNNNNNAp, 3'-F2-NNNNNNGp. 3'-F3-NNNNNNCp and 3'-F4-NNNNNNTp (where "p" is a phosphate available for ligation). In yet another example, a set of fluorophore-labeled 7-mer probes for identifying a base three bases into a target nucleic acid from an interspersed adaptor may have the following structure: 3'-F1-NNNNANNp, 3'-F2-NNNNGNNp. 3'-F3-NNNNCNNp and 3'-F4-NNNNTNNp. To the extent that the ligase discriminates for complementarity at that queried position, the fluorescent signal provides the identity of that base.

After performing the ligation and four-color imaging, the anchor: 8-mer probe complexes are stripped and a new cycle is begun. With T4 DNA ligase, accurate sequence information can be obtained as far as six bases or more from the ligation junction, allowing access to at least 12 bp per adaptor (six bases from both the 5' and 3' ends), for a total of 48 bp per 4-adaptor DNB, 60 bp per 5-adaptor DNB and so on.

Figure 5:
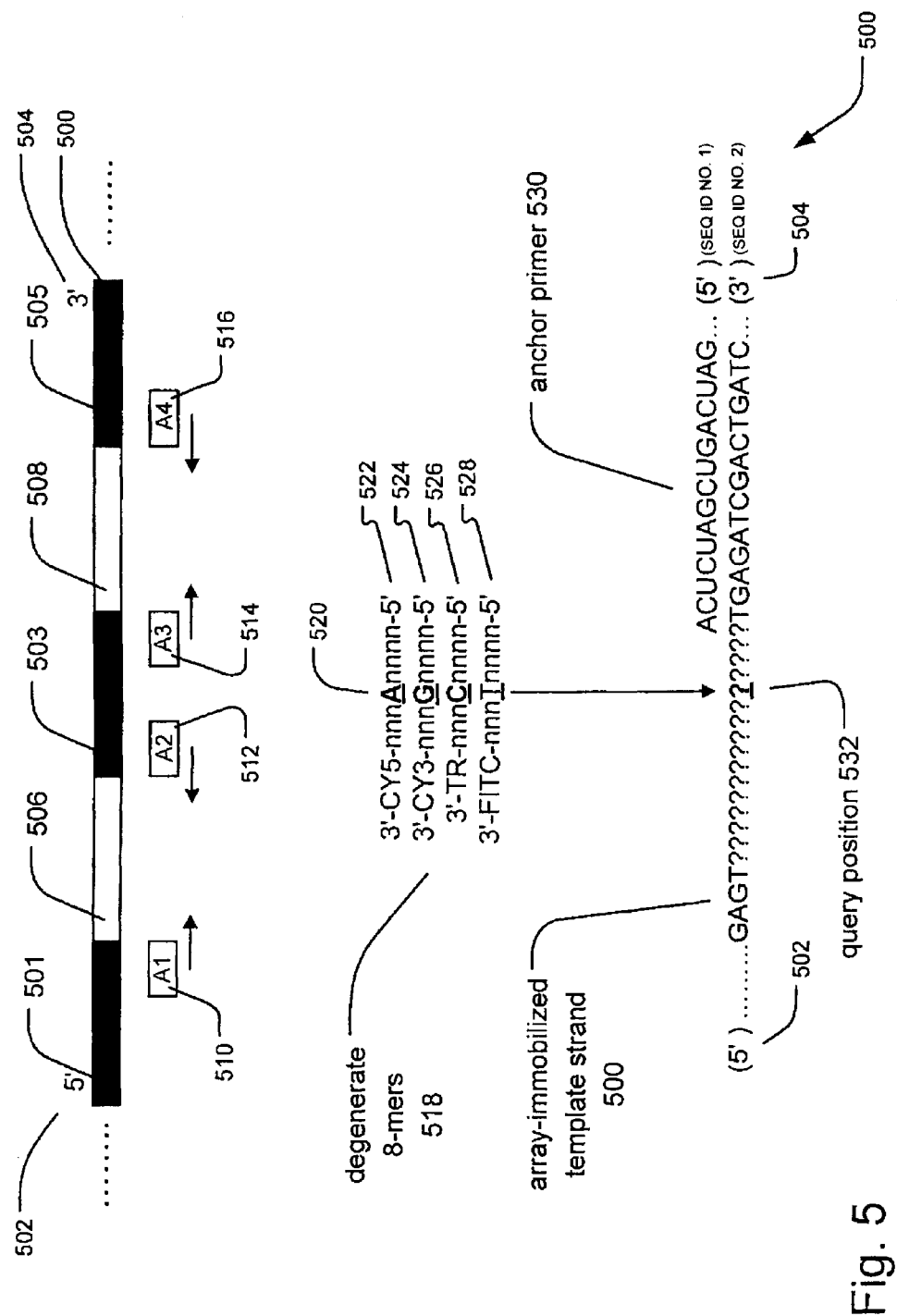
FIG. 5 is a schematic illustration of the components that may be used in an exemplary sequencing-by-ligation technique.

FIG. 5 is a schematic illustration of the components that may be used in an exemplary sequencing-by-ligation technique. A construct 500 is shown with a stretch of target nucleic acid to be analyzed interspersed with three adaptors, with the 5' end of the stretch shown at 502 and the 3' end shown at 504. The target nucleic acid portions are shown at 506 and 508, with adaptor 1 shown at 501, adaptor 2 shown at 503 and adaptor 3 shown at 505. Four anchors are shown: anchor A1 (510), which binds to the 3' end of adaptor 1 (501) and is used to sequence the 5' end of target nucleic acid 506; anchor A2 (512), which binds to the 5' end of adaptor 2 (503) and is used to sequence the 3' end of target nucleic acid 506; anchor A3 (514), which binds to the 3' end of adaptor 2 (503) and is used to sequence the 5' end of target nucleic acid 508; and anchor A4 (516), which binds to the 5' end of adaptor 3 (505) and is used to sequence the 3' end of target nucleic acid 508.

Depending on which position that a given cycle is aiming to interrogate, the 8-mer probes are structured differently. Specifically, a single position within each 8-mer probe is correlated with the identity of the fluorophore with which it is labeled. Additionally, the fluorophore molecule is attached to the opposite end of the 8-mer probe relative to the end targeted to the ligation junction. For example, in the graphic shown here, the anchor 530 is hybridized such that its 3' end is adjacent to the target nucleic acid. To query a position five bases into the target nucleic acid, a population of degenerate 8-mer probes shown here at 518 may be used. The query position is shown at 532. In this case, this correlates with the fifth nucleic acid from the 5' end of the 8-mer probe, which is the end of the 8-mer probe that will ligate to the anchor. In the aspect shown in FIG. 5, the 8-mer probes are individually labeled with one of four fluorophores, where Cy5 is correlated with A (522), Cy3 is correlated with G (524), Texas Red is correlated with C (526), and FITC is correlated with T (528).

Many different variations of cPAL or other sequencing-by-ligation approaches may be selected depending on various factors such as the volume of sequencing desired, the type of labels employed, the number of different adaptors used within each library construct, the number of bases being queried per cycle, how the DNBs are attached to the surface of the array, the desired speed of sequencing operations, signal detection approaches and the like. In the aspect shown in FIG. 5 and described herein, four fluorophores were used and a single base was queried per cycle. It should, however, be recognized that eight or sixteen fluorophores or more may be used per cycle, increasing the number of bases that can be identified during any one cycle. The degenerate probes (in FIG. 5, 8-mer probes) can be labeled in a variety of ways, including the direct or indirect attachment of radioactive moieties, fluorescent moieties, colorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka (2002), *Ann. Clin. Biochem.,* 39: 114-129; and Haugland (2006), *Handbook of Fluorescent Probes and Research Chemicals,* 10th Ed. (Invitrogen/Molecular Probes, Inc., Eugene); Keller and Manak (1993), *DNA Probes,* 2nd Ed. (Stockton Press, New York, 1993); and Eckstein (1991), Ed., *Oligonucleotides and Analogues: A Practical Approach* (IRL Press, Oxford); and the like.

In one aspect, one or more fluorescent dyes are used as labels for the oligonucleotide probes. Labeling can also be carried out with quantum dots, as disclosed in the following patents and patent publications, incorporated herein by reference: 6,322,901; 6,576,291; 6,423,551; 6,251,303; 6,319,426; 6,426,513; 6,444,143; 5,990,479; 6,207,392; 2002/0045045; 2003/0017264; and the like. Commercially available fluorescent nucleotide analogues readily incorporated into the degenerate probes include, for example, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red, the Cy fluorophores, the Alexa Fluor® fluorophores, the BODIPY® fluorophores and the like. FRET tandem fluorophores may also be used. Other suitable labels for detection oligonucleotides may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr) or any other suitable label.

Imaging acquisition may be performed by methods known in the art, such as use of the commercial imaging package Metamorph. Data extraction may be performed by a series of binaries written in, e.g., C/C++, and base-calling and read-mapping may be performed by a series of Matlab and Perl scripts. As described above, for each base in a target nucleic acid to be queried (for example, for 12 bases, reading 6 bases in from both the 5' and 3' ends of each target nucleic acid portion of each DNB), a hybridization reaction, a ligation reaction, imaging and a primer stripping reaction is performed. To determine the identity of each DNB in an array at a given position, after performing the biological sequencing reactions, each field of view ("frame") is imaged with four different wavelengths corresponding to the four fluorescent, e.g., 8-mer probes used. All images from each cycle are saved in a cycle directory, where the number of images is 4× the number of frames (for example, if a four-fluorophore technique is employed). Cycle image data may then be saved into a directory structure organized for downstream processing.

Data extraction typically requires two types of image data: bright field images to demarcate the positions of all DNBs in the array; and sets of fluorescence images acquired during each sequencing cycle. The data extraction software identifies all objects with the bright field images, then for each such object, computes an average fluorescence value for each sequencing cycle. For any given cycle, there are four datapoints, corresponding to the four images taken at different wavelengths to query whether that base is an A, G, C or T. These raw base-calls are consolidated, yielding a discontinuous sequencing read for each DNB. The next task is to match these sequencing reads against a reference genome.

Information regarding the reference genome may be stored in a reference table. A reference table may be compiled using existing sequencing data on the organism of choice. For example human genome data can be accessed through the National Center for Biotechnology Information at ftp.ncbi.nih.gov/refseq/release, or through the J. Craig Venter Institute at http://www.jcvi,org/researchhuref/. All or a subset of human genome information can be used to create a reference table for particular sequencing queries. In addition, specific reference tables can be constructed from empirical data derived from specific populations, including genetic sequence from humans with specific ethnicities, geographic heritage, religious or culturally-defined populations, as the variation within the human genome may slant the reference data depending upon the origin of the information contained therein.

In an alternative aspect of the claimed invention, parallel sequencing of the target nucleic acids in the DNBs on a random array is performed by combinatorial sequencing-by-hybridization (cSBH), as disclosed by Drmanac in U.S. Pat. Nos. 6,864,052; 6,309,824; and 6,401,267. In one aspect, first and second sets of oligonucleotide probes are provided, where each set has member probes that comprise oligonucleotides having every possible sequence for the defined length of probes in the set. For example, if a set contains probes of length six, then it contains 4096 (46) probes. In another aspect, first and second sets of oligonucleotide probes comprise probes having selected nucleotide sequences designed to detect selected sets of target polynucleotides. Sequences are determined by hybridizing one probe or pool of probes, hybridizing a second probe or a second pool or probes, ligating probes that form perfectly matched duplexes on their target sequences, identifying those probes that are ligated to obtain sequence information about the target nucleic acid sequence, repeating the steps until all the probes or pools of probes have been hybridized, and determining the nucleotide sequence of the target nucleic acid from the sequence information accumulated during the hybridization and identification processes.

In yet another alternative aspect, parallel sequencing of the target nucleic acids in the DNBs is performed by sequencing-by-synthesis techniques as described in U.S. Pat. Nos. 6,210,891; 6,828,100, 6,833,246; 6,911,345; Margulies, et al. (2005), *Nature* 437:376-380 and Ronaghi, et al. (1996), *Anal. Biochem.* 242:84-89. Briefly, modified pyrosequencing, in which nucleotide incorporation is detected by the release of an inorganic pyrophosphate and the generation of photons, is performed on the DNBs in the array using sequences in the adaptors for binding of the primers that are extended in the synthesis.

Adaptor Insertion and Structure

Figure 6:
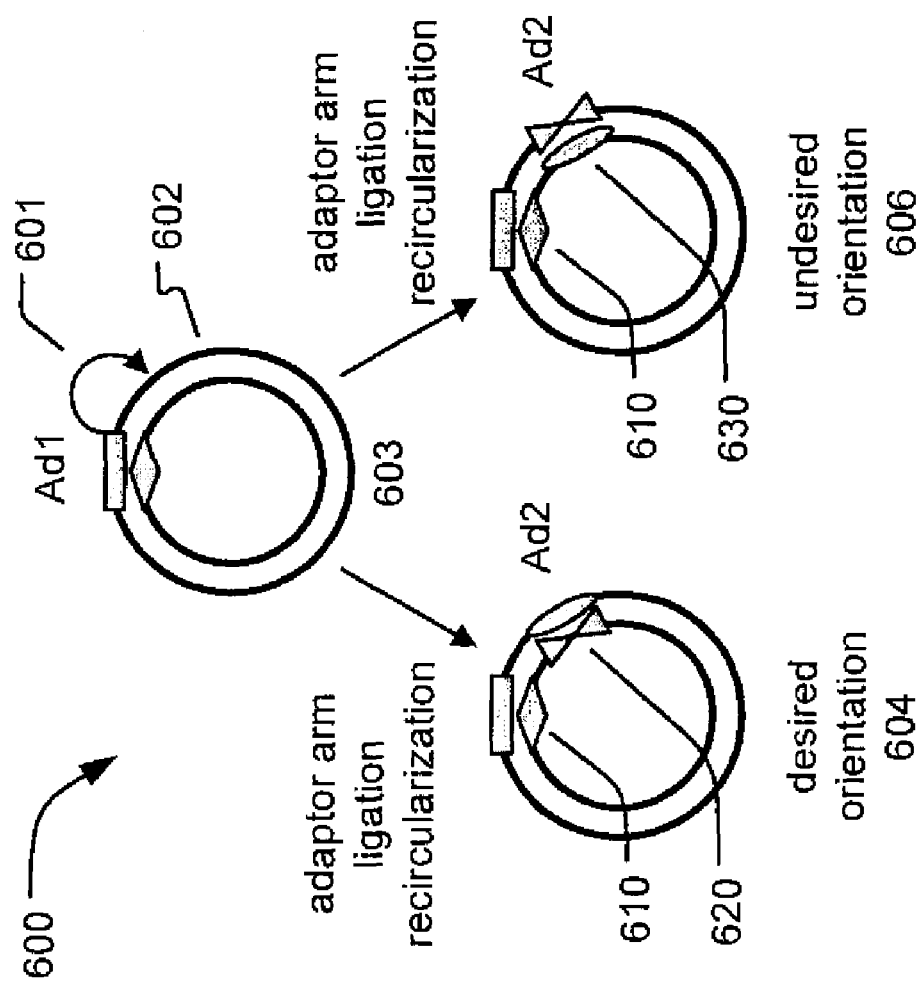
FIG. 6 is a schematic illustration of an insertion of a second adaptor relative to a first adaptor in a nucleic acid library construct.

FIG. 6 is a schematic illustration of an insertion of a second adaptor relative to a first adaptor in a nucleic acid library construct. Again, process 600 begins with circular library construct 602, having an inserted first adaptor 610. First adaptor 610 has a specific orientation, with a rectangle identifying the "outer strand" of the first adaptor and a diamond identifying the "inner strand" of the first adaptor (Ad1 orientation 610). A Type IIs restriction endonuclease site in the first adaptor 610 is indicated by the tail of arrow 601, and the site of cutting is indicated by the arrow head. Process 603 comprises cutting with the Type IIs restriction endonuclease, ligating first and second adaptor arms of a second adaptor, and recircularization. As can be seen in the resulting library constructs 604 and 606, the second adaptor can be inserted in two different ways relative to the first adaptor. In the desired orientation 604, the oval is inserted into the outer strand with the rectangle, and the bowtie is inserted into the inner strand with the diamond (Ad2 orientation 620). In the undesired orientation the oval is inserted into the inner strand with the diamond and the bowtie is inserted into the outer strand with the rectangle (Ad2 orientation 630).

Figure 7:
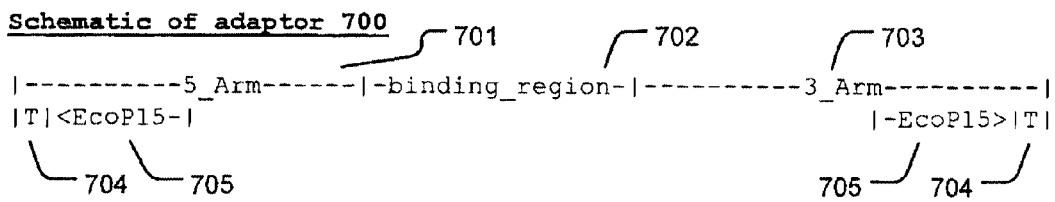
FIG. 7 is a schematic representation of components of an exemplary adaptor useful for selecting insertion orientation.
Figure 7:
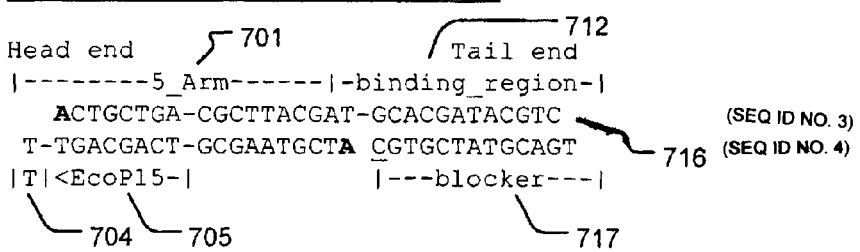
Figure 7:
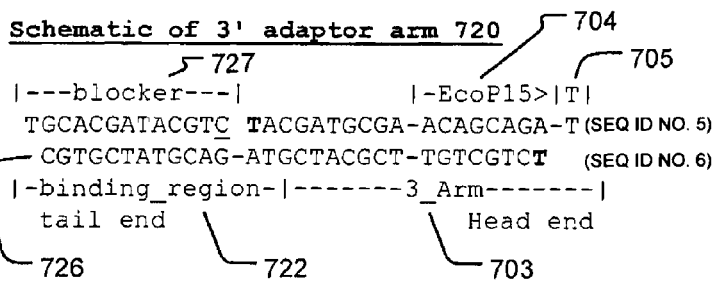

FIG. 7 is a schematic representation of components of an exemplary adaptor useful for selecting insertion orientation. A basic schematic of an adaptor is shown at 700. The adaptor comprises a 5' arm 701, a double-stranded region 702 and a 3' arm 703. Both the 5' and the 3' arms have a "T tail" 704 and a Type IIs restriction endonuclease site 705 (here, EcoP15). The binding region 702 is the region where the two arms of the adaptor come together to be ligated in the circularization process (305 of FIG. 3). Structure 710 is the 5' arm of adaptor 700. Again, T tail 704 and the EcoP15 site 705 are shown, as well as the 5' anchor region 701 and the binding region 712. Structure 720 is the 3' arm of adaptor 700. Note the T tail 704 and the EcoP15 site 705, as well as the 3' anchor region 703 and the binding region 722. In the 5' arm, the binding region 712 is complementary to the binding region 722 of the 3' arm.

Because the aspects of the claimed invention work optimally when library constructs are of a desired size and limited target nucleic acid sequence, it is preferred that throughout the library construction process the circularization reactions occur intramolecularly. That is, that the separate constructs of the library that are generated in the library construct assembly cycle (as shown in FIG. 3) do not ligate to one another. Also, it is preferred that only one set of adaptor arms for each adaptor used in the library construction process be included per target nucleic acid/adaptor construct. Thus, blocking oligos 717 and 727 are used to block the binding regions 712 and 722 regions, respectively. Blocker oligonucleotide 717 is complementary to binding sequence 716, and blocker oligonucleotide 727 is complementary to binding sequence 726. In the schematic illustrations of the 5' adaptor arm and the 3' adaptor arm, the underlined bases are ddC and the bolded font bases are phosphorylated. Blocker oligonucleotides 717 and 727 are not covalently bound to the adaptor arms, and can be "melted off" after ligation of the adaptor arms to the library construct and before circularization; further, the dideoxy nucleotide (here, ddC or alternatively a different non-ligatable nucleotide) prevents ligation of blocker to adaptor. In addition or as an alternative, in some aspects, the blocker oligo-adaptor arm hybrids contain a one or more base gap between the adaptor arm and the blocker to reduce ligation of blocker to adaptor. In some aspects, the blocker/binding region hybrids have $T_m$s of about 37° C. to enable easy melting of the blocker sequences prior to tail to tail ligation (circularization).

Adaptor structure 730 is a schematic of the final adaptor, where N is an unspecified base, a numeral "1" specifies bases added to disrupt the palindrome (i.e., the EcoP15 site is flanked by A's to isolate the 6-base palindrome formed by the EcoP15 sites on the two arms of the adaptor), numeral "2" specifies bases that correspond to the ddC in the blocker oligonucleotides, numeral "3" specifies the EcoP15 site (CT-GCTG) and numeral "4" specifies the T bases designated for TA ligation to the A tailed target nucleic acid. The adaptor shown as 900 and detailed at 930 would, in some aspects, be appropriate for a first adaptor to be added in the construction of a library. Adaptors added subsequently would, in some aspects, have a single Type IIs restriction endonuclease site rather than two sites. The methods disclosed herein allow for use of a single Type IIs restriction endonuclease to be employed in the construction of the library, if desired. In some aspects, however, there may be one or two Type IIs restriction endonuclease sites in the first adaptor, where the two Type IIs restriction endonuclease sites may be the same or different. However, the successively-added adaptors would have only a single Type IIs restriction endonuclease site and these sites may be the same for the second, third, and so on, adaptors. Exemplary Type IIs restriction endonucleases include, but are not limited to, Eco57M I, Mme I, Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I, Taq II, and the like.

In some aspects, the adaptors when assembled have a total length of about 50 nucleotides. As shown above, in some aspects, the adaptors are ligated to the target nucleic acid as two adaptor arms, where each adaptor arm comprises two adaptor oligos (the two complementary strands) and one blocker oligo. As shown, the 5' ends of all four adaptor arm oligos are phosphorylated to support ligation to the insert and tail-to-tail ligation of 5' to 3' adaptor arms. As shown, the 5' and 3' adaptor arms have 3' overhangs at the adaptor-target nucleic acid ligation junctions, to enable ligation to an A-tailed insert, and to suppress head-to-head adaptor arm ligation. Also as shown, the 5' and 3' adaptor arms have Type IIs restriction endonuclease recognition sites oriented to enable cleavage of the adjacent target nucleic acid. In addition, in some aspects, the adaptors comprise methylase blocker sites, as described in detail infra.

Again, the adaptor construct shown in FIG. 7 would be, in some aspects, appropriate for a first adaptor to be inserted into a library construct because it contains two Type IIs restriction endonuclease recognition sites. Subsequently inserted adaptors would, in some aspects, comprise a single Type IIs restriction endonuclease recognition site oriented to enable cleavage of the adjacent target nucleic acid. Additionally, in preferred aspects, the 5' and 3' adaptor arms have anchor binding sites to enable sequencing of adjacent target nucleic acids. The anchor binding sites in some aspects overlap with the respective Type IIs restriction endonuclease recognition site(s); however, in other aspects the anchor binding sites do not overlap with the Type IIs restriction endonuclease recognition site(s).

Figure 8:
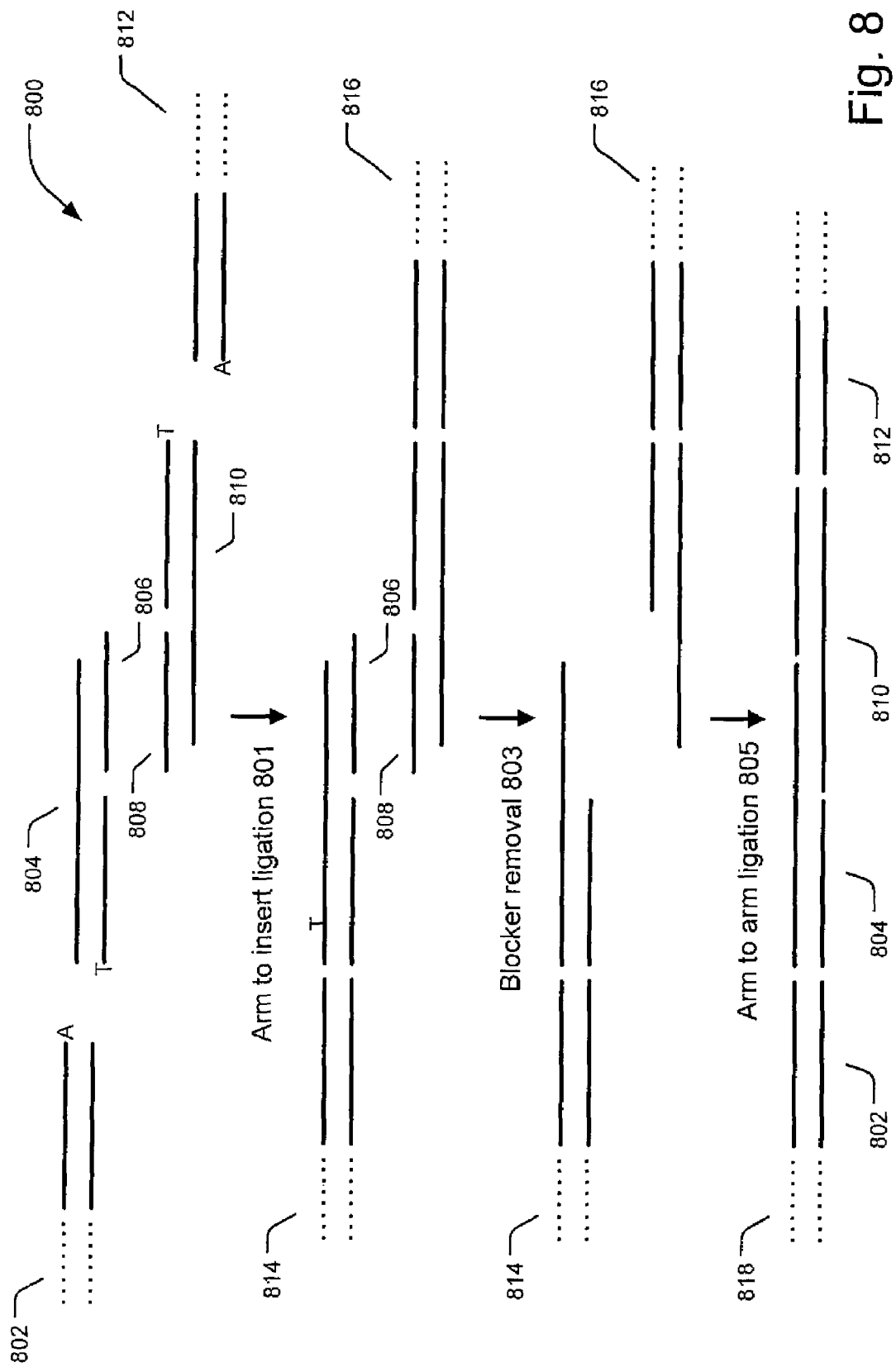
FIG. 8 is a schematic representation of adaptor insertion allowing subsequent circularization of the target/adaptor construct.
Figure 10:
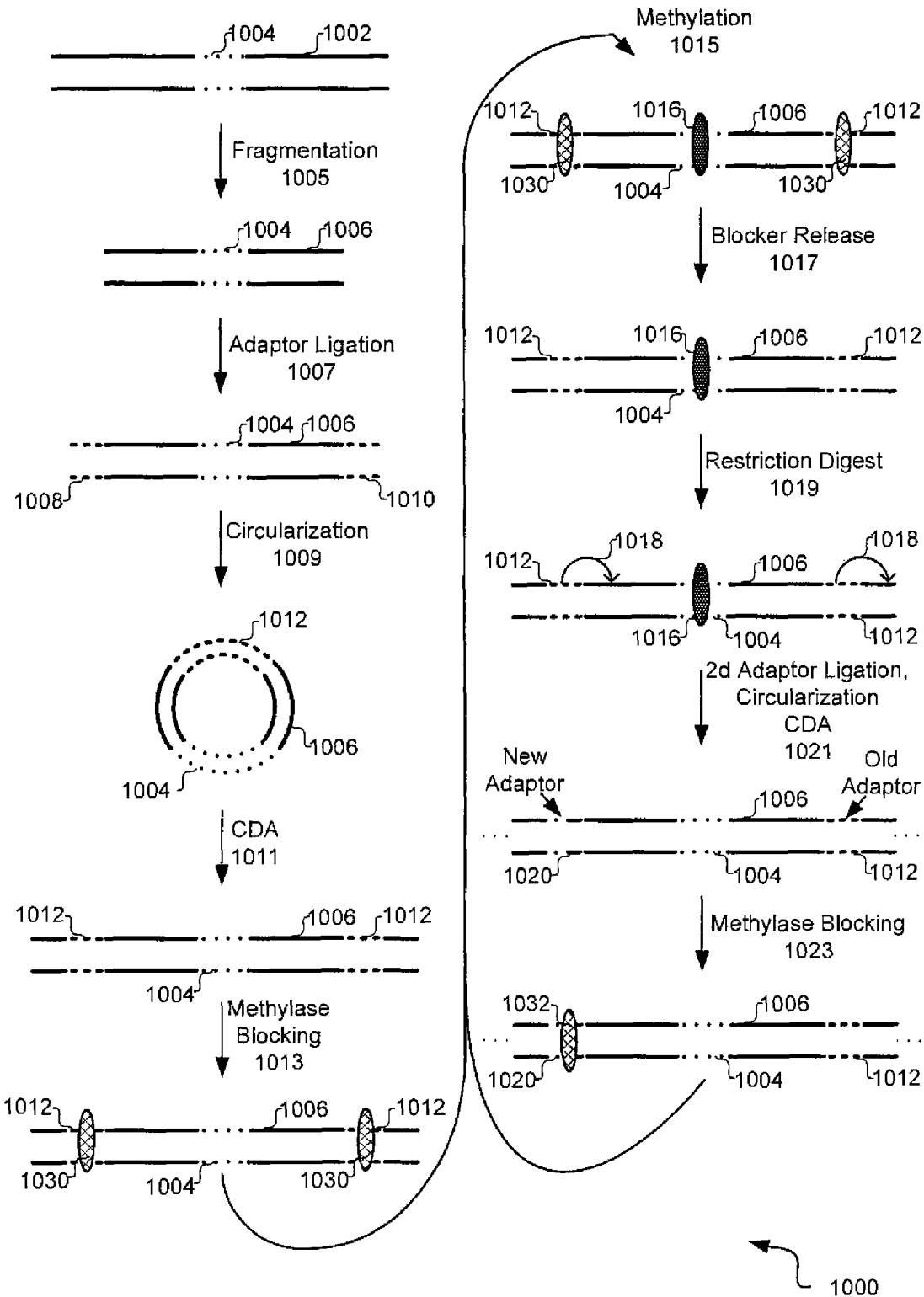
FIG. 10 is a schematic representation of a process where a desired position of a second adaptor relative to a first adaptor is selected using sequence-specific methylation and sequence specific methylase blockers.

FIG. 8 is a schematic representation of adaptor insertion allowing subsequent circularization of the target/adaptor construct that may be used in some aspects of the invention such as the aspect illustrated in FIG. 10. The portion of the library construct seen in FIG. 8 is adaptor-centric, showing target nucleic acid at 802 and 812, a 5' adaptor arm at 804, a 5' adaptor arm blocking oligo at 806, a 3' adaptor arm at 810, and a 3' adaptor arm blocking oligo at 808. The T tail of the adaptor arms 804 and 810 and the A tail of the target nucleic acids 802 and 812 are indicated. In process 801, the adaptor arms are ligated to the target nucleic acid resulting in target nucleic acid/5' adaptor arm structure 814, and target nucleic acid/3' adaptor arm structure 816, with blocking oligos 806 and 808 still hybridized to the target nucleic acid/adaptor arm structures. In process 803, the blockers are removed by melting, and, in preferred aspects under dilute conditions to favor intramolecular ligation of process 805. The resulting structure is seen at 818. FIG. 8 illustrates the process of adaptor arm ligation featuring blocking oliogs; however, other methods may be used to block ligation-creating concatemers of adaptor arms or of library constructs, including using adaptor arms that comprise a restriction site, preferably a site for a restriction endonuclease that cuts asymmetrically, such as Ava I. Alternatively, the adaptor arms may comprise one or more uracil bases that can be selectively cleaved using uracil-DNA glycosylase enzyme (Krokan, et al., (1997) *Biochem. J.* 325:1-16) with the resulting fragments then being melted off in the same way the blocker oligo is melted off.

Restriction Site Protection by Methylation

Figure 9:
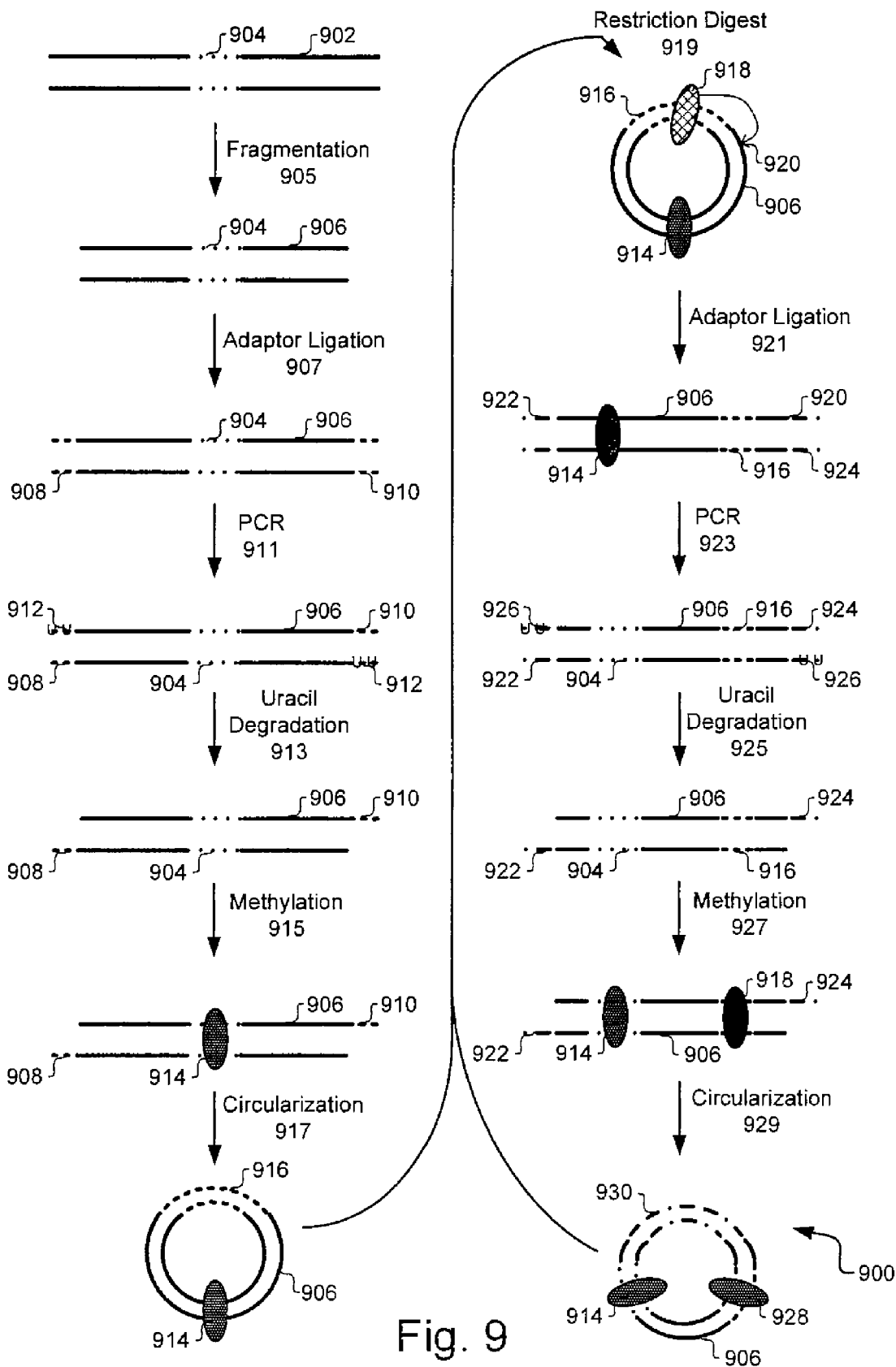
FIG. 9 is a schematic illustration of a process where a desired position of a second adaptor relative to a first adaptor is selected using sequence-specific methylation and uracil degradation.

FIG. 9 is a schematic illustration of a process where a desired position of a second adaptor relative to a first adaptor is selected using methylation and uracil degradation. FIG. 9 shows genomic DNA of interest 902 having a Type IIs restriction endonuclease recognition site at 904. The genomic DNA is fractionated or fragmented in process 905 to produce fragments 906 having a Type IIs restriction endonuclease recognition site 904. Adaptor arms 908 and 910 are ligated to fragment 906 in process 907 (in some aspects, as illustrated and described in FIGS. 7 and 8 and the associated text, supra). Fragment 906 with first and second adaptor arms 908 and 910 (a library construct) are amplified by PCR in process 911, using uracil-modified primers 912 complementary to adaptor arms 908 and 910. The primers generate a PCR product with uracils at or close to the Type IIs restriction endonuclease recognition site. In process 913, the uracils are specifically degraded using, e.g., uracil-DNA glycosylase enzyme (Krokan, et al., (1997) *Biochem. J.* 325:1-16), leaving a PCR product that is single-stranded in the Type IIs restriction endonuclease recognition site region. As shown, uracil incorporation and degradation may be used to render the Type IIs restriction endonuclease recognition site single-stranded; however, as described previously, other methods may be employed to render these regions single-stranded including use of 3' or 5' exonucleases in a limited digest.

In process 915, a sequence-specific methylase is used to methylate bases in each double-stranded Type IIs restriction endonuclease recognition site (here, there is methylation 914 of the Type IIs restriction endonuclease recognition site 904), to protect these sites from Type IIs restriction endonuclease recognition. However, the single-stranded Type IIs restriction endonuclease recognition sites in first and second adaptor arms 908 and 910 are not methylated, and, once circularized and ligated 917, the Type IIs restriction endonuclease recognition site re-forms 916 such that this Type IIs restriction endonuclease recognition site is available for restriction. When selecting the methylase and the Type IIs restriction endonucleases for this process, it is necessary that the two enzymes recognize the same sequence or that one enzyme recognizes a subsequence (sequence within the sequence) of the other enzyme. The circularized construct is then cut with the Type IIs restriction endonuclease in process 919 where the Type IIs restriction endonuclease recognition site is indicated at 918 and the construct is cut at 920, resulting in a linearized construct available for ligation of a second set of adaptor arms to be added to the construct in process 921.

Ligation process 921 adds first 922 and second 924 adaptor arms of the second adaptor to the linearized construct, and a second amplification is performed by PCR at process 923, again using uracil-modified primers 926 complementary to adaptor arms 922 and 924. As before, the primers generate a PCR product with uracils close to the Type IIs restriction endonuclease recognition site. In process 925, the uracils are specifically degraded leaving a PCR product that is single-stranded in the Type IIs restriction endonuclease recognition site region of the first and second adaptor arms 922 and 924 of the second adaptor. In process 927, the sequence-specific methylase again is used to methylate bases in the double-stranded Type IIs restriction endonuclease recognition sites in the target nucleic acid fragment (again, there is methylation 914 of the Type IIs restriction endonuclease recognition site 904) and in the Type IIs restriction endonuclease recognition site of the first adaptor 928 protecting these sites from Type IIs restriction endonuclease recognition. The methylated construct is then circularized at process 929, where the Type IIs restriction endonuclease recognition site in the first and second arms 922 and 924 of the second adaptor is re-formed 930 and the process is repeated where the circularized construct is cut again with the Type IIs restriction endonuclease in process 919 to generate another linearized construct (this one with first and second adaptors already added) available for ligation of a third pair of adaptor arms to the construct. The process can be repeated to add as many adaptors as are desired. As shown here, the first added adaptor had one Type IIs restriction endonuclease recognition site; however, in other aspects, the first added adaptor may have two Type IIs restriction endonuclease recognition sites to allow for precise selection of target nucleic acid size for the construct.

FIG. 10 is a schematic representation of a process where a desired position of a second adaptor relative to a first adaptor is selected using methylation and sequence-specific methylase blockers. FIG. 10 shows genomic DNA of interest (target nucleic acid) 1002 having a Type IIs restriction endonuclease recognition site at 1004. The genomic DNA is fractionated or fragmented in process 1005 to produce fragment 1006 having a Type IIs restriction endonuclease recognition site 1004. Adaptor arms 1008 and 1010 are ligated to fragment 1006 in process 1007. Fragment 1006 with adaptor arms 1008 and 1010 (a library construct) is circularized in process 1009 and amplified by circle dependent amplification in process 1011, resulting in a highly-branched concatemer of alternating target nucleic acid fragments 1006 (with the Type IIs restriction endonuclease recognition site at 1004) and first adaptors 1012.

In process 1013, a sequence-specific methylase blocker 1030 such as a zinc finger is used to block methylation in specific Type IIs restriction endonuclease recognition sites in the library construct. Here, the Type IIs restriction endonuclease recognition sites in adaptor arms 1012 and 1014 are blocked by methylase blocker 1030. When selecting the methylase blocker and the Type IIs restriction endonucleases for this process, it is not necessary that the two entities recognize the same site sequence or that one entity recognizes a subsequence of the other entity. The blocker sequences may be up- or downstream from the Type IIs restriction endonuclease recognition site, but are of a configuration that the methylase blocker blocks the site (such as with a zinc finger or other nucleic acid binding protein or other entity). In process 1015, unprotected Type IIs restriction endonuclease recognition sites in the construct are methylated—here, methylation 1016 of the Type IIs restriction endonuclease recognition site 1004)—protecting these sites from Type IIs restriction endonuclease recognition. However, the Type IIs restriction endonuclease recognition sites in adaptors 1012 and 1014 are not methylated due to the presence of the methylase blocker.

At process 1017, the methylase blocker is released from the library construct, resulting in a library construct where the Type IIs restriction endonuclease recognition site in adaptors 1012 are available for recognition and restriction 1018, and the Type IIs restriction endonuclease recognition site in the genomic fragment 1004, is not. The methylated construct is then ligated to an second pair of adaptor arms, circularized, and amplified via circle dependent amplification at process 1021, resulting in a concatemer of alternating target nucleic acid fragments 1006 (with the Type IIs restriction endonuclease recognition site at 1004), first adaptors 1012 and second adaptors 1020. Next, in process 1023, methylase blocking is performed again, this time with a methylase blocker that recognizes a site in the second adaptor 1020 to block methylation of the Type IIs restriction endonuclease recognition site in the second adaptor 1020, but not the other Type IIs restriction endonuclease recognition sites in the construct (i.e., the Type IIs restriction endonuclease recognition site 1004 in the fragment and the Type IIs restriction endonuclease recognition site in first adaptor 1012). The process then continues with methylation 1015, and further adaptor arms are added, if desired. Different methylase blocker sites are used in each different adaptor, allowing for sequence-specific methylase blocking throughout the process. Though FIGS. 9 and 10 show insertion of a second adaptor in relation to a first, it should be understood that the process is applicable to adaptors added subsequently to the second adaptor, creating library constructs with up to four, six, eight, ten or more inserted adaptors.

The inability to control the orientation of adaptors with respect to one another can have a number of undesired consequences. The presence of adaptors in both orientations in a population of target nucleic acid/adaptor library constructs may require multiple sequencing primers in each sequencing reaction to enable sequencing regardless of the orientation of a given adaptor. In addition, analysis of sequence data collected from multiple adaptors of unspecified orientation may require either determination of the orientation of each adaptor or consideration of all possible combinations of adaptor orientation during assembly. Thus, in addition to directing the relative position of inserted adaptors to one another, it is desirable in some aspects to direct the relative orientation of subsequently-inserted adaptors as well.

Figure 11:
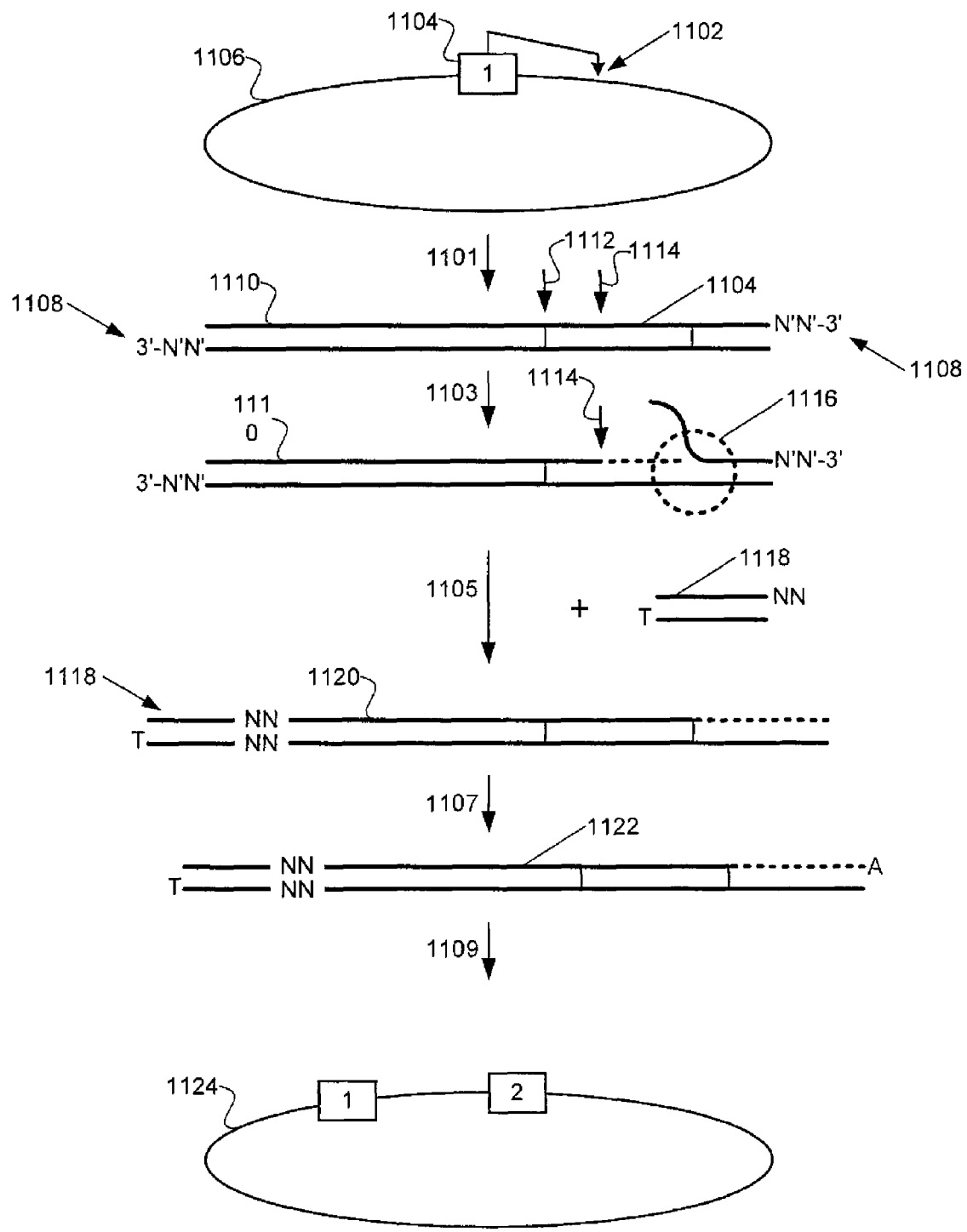
FIG. 11 is a schematic representation of a process where a nick translation-type process is used to control the orientation with which a second adaptor is inserted with respect to a first adaptor.

FIG. 11 shows one method for inserting adaptors in an orientation-specific manner with respect to one another that can be used in conjunction with the methylase protection methods for positioning adaptors described herein. For example, after restriction digest 919 and before adaptor ligation 921 of FIG. 9, and after the restriction digest process 1019 and before the second adaptor ligation, circularization and CDA processes 1021 of FIG. 10, the "nick translation" type process shown in FIG. 11 can be performed. In the case of the process shown in FIG. 9, a library construct (substantially similar to 1106 in FIG. 11) has been formed that is circular and has an interspersed adaptor 916 (substantially similar to 1104 in FIG. 11), with a restriction endonuclease recognition site at 918 (tail of the arrow in FIG. 11), and a site of restriction at 920 (1102 of FIG. 11). In FIG. 10, the library construct is not circularized, but is a branched concatemer of alternating target nucleic acid fragments 1006 (with restriction endonuclease recognition sites 1004) and adaptors 1012; however, the nick translation type process shown in FIG. 11 may be performed on such a library construct configuration as well.

The library constructs with an inserted first adaptor are digested by a restriction endonuclease (process 1101)—in preferred aspects, a Type IIs restriction endonuclease—that cuts the target nucleic acid to render 3' nucleotide overhangs 1108. In FIG. 11, two nucleotides (NN-3') 1108 are shown, though the number of overhanging nucleotides varies in alternative aspects. The library construct 1110 is linearized, with the first inserted adaptor shown at 1104. The first inserted adaptor 1104 is engineered such that it comprises either a nick 1112 at the boundary of the adaptor fragment or it comprises the recognition site for a nicking endonuclease that permits the introduction of a nick 1114 at the interior of the adaptor. In either case, library construct 1110 is treated 1103 with a polymerase 1116 that can extend the upper strand from nick 1112 or 1114 to the end of the lower strand of library construct 1110 to form a strand having a 3' overhang at one end and a blunt end at the other. To this library construct 1110, a second adaptor 1118 is ligated in process 1105, where the second adaptor 1118 has a degenerate nucleotide overhang at one end and a single 3' nucleotide (e.g., dT) overhang at the other end to form library construct 1120. Library construct 1120 is then treated (e.g., with Taq polymerase) in process 1107 to add a 3' dA to the blunt end. Library construct 1122 may then be amplified by PCR (such as shown at process 923 of FIG. 9), with, e.g., uracil-containing primers. Alternatively, library construct 1122 may then be circularized in process 1109 in which case CDA may be performed (such as in step 1021 of FIG. 10). Combining the processes shown in FIG. 9 or 10 with the nick translation type process shown in FIG. 11 allows for selecting both the relative position and relative orientation of subsequently-added adaptors to any adaptors previously inserted into the library constructs.

In alternative embodiments to the nick translation type process to select for orientation, methods for enriching for adaptors added in specific orientations may be performed with the methylation/protection methods of the invention claimed. Such processes are described in U.S. Ser. No. 60/864,992 filed Nov. 9, 2006; U.S. Ser. No. 11/943,703, filed Nov. 2, 2007; U.S. Ser. No. 11/943,697, filed Nov. 2, 2007; U.S. Ser. No. 11/943,695, filed Nov. 2, 2007; and PCT/U.S.07/835,540; filed Nov. 2, 2007, all of which are incorporated by reference in their entirety.

EXAMPLES

A Tailing: Samples of 100 ng of fragmented genomic DNA were prepared in Thermopol buffer, with dATP and Taq polymerase added. The samples were then incubated at 70° C. for 60 minutes and cooled to 4° C. The samples were then purified by Qiagen MinElute columns.

Adaptor annealing: The A tailed fragmented genomic DNA samples were mixed with T tailed adaptors and blocking oligos in a buffer containing NaCl, Tris and EDTA. The samples were then heated to 95° C. for 5 minutes and then allowed to cool to room temperature.

Adaptor ligation: The annealed adaptor/genomic DNA samples were mixed with HB ligation buffer and T4 ligase. The samples were then incubated at 14° C. for two hours, 70° C. for 10 minutes (to inactivate the T4 enzyme and remove the blocking oligos) and cooled to 4° C. The samples were then purified by Qiagen MinElute columns.

Adaptor circularization: The linear fragmented genomic DNAs now flanked by first and second arms of an adaptor were circularized by incubation in epicenter buffer and T4 Ligase at 14° C. for 14 hours. The samples were then heat inactivated at 70° C. for 10 minutes and then cooled to 4° C.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Changes in detail or structure may be made without departing from the basic elements of the present technology as defined in the following claims. In the claims of any corresponding utility application, unless the term "means" is used, none of the features or elements recited therein should be construed as means-plus-function limitations pursuant to 35 U.S.C. §112, ¶6.

What is claimed is:

1. A method for selectively activating a recognition site for a Type IIs restriction endonuclease in a nucleic acid sequence, the method comprising:

(a) providing a nucleic acid sequence comprising first and second recognition sites for a Type IIs restriction endonuclease;

(b) amplifying the nucleic acid sequence using a uracil-containing primer that has a sequence that is complementary to the first recognition site, thereby producing an amplified nucleic acid sequence comprising a first recognition site for a Type IIs restriction endonuclease comprising, one or more uracils at or near the first recognition site, and a second recognition site for a Type IIs restriction endonuclease;

(c) degrading said one or more uracils at or near the first recognition site, thereby producing a single-stranded region in the first recognition site and protecting the first recognition site from methylation by a methylase that methylates unprotected recognition sites for the Type IIs restriction endonuclease;

(d) methylating the second recognition site with the methylase, inhibiting digestion of the nucleic acid sequence by the Type IIs restriction endonuclease resulting from recognition of the second recognition site; and (e) making the single-stranded region double-stranded such that the Type IIs restriction endonuclease can recognize the first recognition site and digest the nucleic acid sequence.

2. A method of positioning a second adaptor with respect to a first adaptor in a nucleic acid template construct, said method comprising:

(a) providing a first linear construct, wherein said first linear construct comprises a target nucleic acid and a first adaptor, and wherein said first adaptor comprises a first recognition site for a first Type IIs restriction endonuclease;

(b) protecting said first recognition site from inactivation;
(c) inactivating unprotected restriction endonuclease recognition sites in said first linear construct;
(d) circularizing said first linear construct to form a first circular construct;
(e) applying said first Type IIs restriction endonuclease to said first circular construct to form a second linear construct, wherein said second linear construct comprises said first adaptor inserted within said target nucleic acid;
(f) ligating a second adaptor to said second linear construct to form said nucleic acid template construct, wherein said second adaptor comprises a second recognition site for a second Type IIs restriction endonuclease;
thereby positioning said second adaptor with respect to said first adaptor in said nucleic acid template construct.

3. The method of claim 2, wherein said protecting step (b) comprises rendering said first recognition site single-stranded.

4. The method of claim 3, wherein said rendering said first recognition site single-stranded comprises:
(a) amplifying said first linear construct with uracil-modified primer complementary to said first adaptor to produce first uracil-modified linear constructs; and
(b) degrading uracils in said first uracil-modified linear constructs, thereby rendering said first recognition site single-stranded.

5. The method of claim 2 further comprising:
(a) circularizing said second linear construct to form a second circular construct;
(b) protecting said second recognition site from inactivation;
(c) inactivating unprotected Type IIs restriction endonuclease recognition sites in said second circular construct;
(d) applying said second restriction endonuclease to said second circular construct to form a second linear construct, wherein said second linear construct comprises said first adaptor and said second adaptor inserted within said target nucleic acid;
(e) ligating a third adaptor to said second linear construct to form a third linear construct;
(f) circularizing said third linear construct, thereby forming said nucleic acid template construct.

6. The method of claim 5, further comprising repeating steps (h) through (l) to insert a desired number of further adaptors, wherein said protecting step is performed on each successively-added adaptor.

7. A method of making a library of circular nucleic acid templates each comprising a target nucleic acid sequence and at least two adaptors, said method. comprising:
(a) providing fragments of genomic nucleic acid;
(b) adding a first arm of a first adaptor to one terminus of a plurality of said fragments;
(c) adding a second arm of a first adaptor to the other terminus of said plurality of said fragments to form first linear constructs, wherein said first and second arms of said first adaptor, when ligated, form said first adaptor and produce a first recognition site for a first Type IIs restriction endonuclease;
(d) protecting said first recognition site in said first linear constructs from inactivation;
(e) inactivating any unprotected first recognition sites present in said first linear constructs;
(f) circularizing said first linear constructs by ligating said first and second adaptor arms to form first circular constructs;
(g) cleaving said first circular constructs with said first Type IIs restriction endonuclease to form second linear constructs comprising said first adaptor inserted within said target nucleic acid, wherein said first Type IIs restriction endonuclease binds to said protected first recognition site and cleaves at a position in said first circular constructs outside of said first adaptor;
(h) adding a first arm of a second adaptor to one terminus of said plurality of said second linear constructs;
(i) adding a second arm of a second adaptor to the other terminus of said plurality of said fragments to form second linear constructs, wherein said first and second arms of said second adaptor, when ligated, form said second adaptor and form a second Type IIs recognition site;
(j) circularizing said second linear constructs by ligating said first and second adaptor arms of said second adaptor to form second circular constructs, thereby making said library of circular nucleic acid templates.

8. The method of claim 7, wherein said fragments are generated by:
(a) isolating said genomic nucleic acid;
(b) fractionating said genomic nucleic acid;
(c) isolating fragments of a desired size; and
(d) modifying the termini of said fragments such that two fragment are unable to ligate to each other, thereby generating said fragments.

9. The method of claim 8, wherein said isolating comprises using gel fractionation.

10. The method of claim 7, wherein said protecting step comprises:
(a) embedding uracils in said first recognition site;
(b) degrading said uracils.

11. The method of claim 10, wherein said inactivating step comprises applying a sequence-specific methylase that is only able to methylate double stranded sequences, wherein said sequence-specific methylase is specific for said first recognition site.

12. The method of claim 10, wherein said embedding comprises amplifying said first linear constructs with uracil-modified primers to produce first linear constructs with uracils embedded in said first recognition site.

13. The method of claim 6, further comprising generating concatemers from said library of circular nucleic acid templates.

14. The method of claim 13, further comprising disposing said concatemers on a surface to form a random array.

15. The method of claim 14, further comprising identifying at least one nucleotide in at least one of said concatemers.

16. The method of claim 15, wherein said at least one nucleotide is adjacent to one of said first, second and third adaptors.

17. The method of claim 15, wherein said identifying comprises:
(i) hybridizing one or more probes from a first set of probes to said concatemer under conditions that permit the formation of perfectly matched duplexes between the one or more probes and complementary sequences on said concatemer;
(ii) hybridizing one or more probes from a second set of probes to said concatemer under conditions that permit the formation of perfectly matched duplexes between the one or more probes and complementary sequences on said concatemer;
(iii) ligating probes from the first and second sets which are hybridized to said concatemer at contiguous sites;
(iv) identifying the sequences of the ligated probes, thereby identifying said at least one nucleotide.

* * * * *

```
                              SEQUENCE LISTING

<160> NUMBER OF SEQ ID NOS: 9

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
acucuagcug acuag                                                          15

<210> SEQ ID NO 2
<211> LENGTH: 35
<212> TYPE: DNA
<213> ORGANISM: Artificial Sequence
<220> FEATURE:
<223> OTHER INFORMATION: Target nucleic acid
<220> FEATURE:
<221> NAME/KEY: misc_feature
<222> LOCATION: (5)...(21)
<223> OTHER INFORMATION: N is A, C, G or T

<400> SEQUENCE: 2
gagtnnnnnn nnnnnnnnnn tgagatcgac tgatc                                    35

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
actgctgacg cttacgatgc acgatacgtc                                          30

<210> SEQ ID NO 4
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 4
ttgacgactg cgaatgctac gtgctatgca gt                                       32

<210> SEQ ID NO 5
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 5
tgcacgatac gtctacgatg cgaacagcag at                                       32

<210> SEQ ID NO 6
<211> LENGTH: 30
<212> TYPE: DNA
<213> ORGANISM: Artificial Sequence
```

```
<220> FEATURE:
<223> OTHER INFORMATION: Synthetic oligonucleotide

<400> SEQUENCE: 6
cgtgctatgc agatgctacg cttgtcgtct                                   30

<210> SEQ ID NO 7
<211> LENGTH: 50
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)...(19)
<223> OTHER INFORMATION: N is A, G, C or T
<220> FEATURE:
<221> NAME/KEY: misc_feature
<222> LOCATION: (21)...(30)
<223> OTHER INFORMATION: N is A, G, C or T
<220> FEATURE:
<221> NAME/KEY: misc_feature
<222> LOCATION: (32)...(41)
<223> OTHER INFORMATION: N is A, G, C or T

<400> SEQUENCE: 7
aactgctgan nnnnnnnnng nnnnnnnnnn cnnnnnnnnn nacagcagat              50

<210> SEQ ID NO 8
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 8
aactgctgac gcttacgatg cacgatacgt ctacgatgcg aacagcaga              49

<210> SEQ ID NO 9
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 9
tgacgactgc gaatgctacg tgctatgcag atgctacgct tgtcgtcta              49
```